United States Patent [19]

Axen et al.

[11] 4,289,893

[45] Sep. 15, 1981

[54] 2,5-INTER-O-PHENYLENE-3,4-DINOR-PGF$_2$ COMPOUNDS

[75] Inventors: Udo F. Axen, Plainwell; John C. Sih, Kalamazoo, both of Mich.

[73] Assignee: The Upjohn Company, Kalamazoo, Mich.

[21] Appl. No.: 165,599

[22] Filed: Jul. 3, 1980

Related U.S. Application Data

[60] Division of Ser. No. 62,443, Jul. 31, 1979, which is a continuation-in-part of Ser. No. 962,845, Nov. 22, 1978, abandoned.

[51] Int. Cl.$^3$ .............................................. C07C 177/00
[52] U.S. Cl. ...................................... 560/55; 562/465
[58] Field of Search .......................... 560/55; 562/465

*Primary Examiner*—Paul J. Killos
*Attorney, Agent, or Firm*—Robert A. Armitage

[57] ABSTRACT

The present invention provides 2,5-inter-o-phenylene-3,4-dinor-PGF$_2$ compounds. These compounds are intermediates for preparing 2,5-inter-o-phenylene-3,4-dinor-prostacyclin analogs, which are useful for pharmacological purposes, e.g., as antithrombotic agents.

1 Claim, No Drawings

2,5-INTER-O-PHENYLENE-3,4-DINOR-PGF$_2$ COMPOUNDS

CROSS REFERENCE TO RELATED APPLICATION

This application is a division of Ser. No. 062,443, filed July 31, 1979, now pending, which is a continuation-in-part of Ser. No. 962,845, filed Nov. 22, 1978, now abandoned.

BACKGROUND OF THE INVENTION

The present invention relates to novel prostacyclin analogs and intermediates for their production. In particular, the present invention relates to prostacyclin intermediates useful in the production of 2,5-inter-o-phenylene-3,4-dinor-prostacyclin analogs. Most particularly the present invention provides 2,5-inter-o-phenylene-3,4-dinor-PGF$_2$ compounds. The preparation and use of the novel compounds is described in Appendix A.

SUMMARY OF THE INVENTION

The present invention particularly provides a prostacyclin intermediate of formula VII

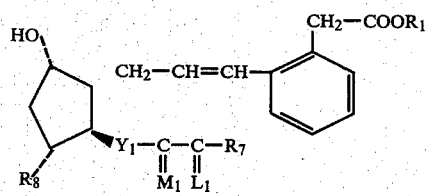

wherein

R$_8$ is hydrogen, hydroxy, or hydroxymethyl; wherein Y$_1$ is (1) trans—CH=CH—,
(2) cis—CH=CH—,
(3) —CH$_2$CH$_2$—, or
(4) —C≡C—, wherein M$_1$ is α-R$_5$:β-OH or α-OH:β-R$_5$, wherein R$_5$ is hydrogen or alkyl with one to 4 carbon atoms, inclusive, wherein L$_1$ is α-R$_3$:β-R$_4$, α-R$_4$:β-R$_3$, or a mixture of α-R$_3$:β-R$_4$ and α-R$_4$:β-R$_3$, wherein R$_3$ and R$_4$ are hydrogen, methyl, or fluoro, being the same or different, with the proviso that one of R$_3$ and R$_4$ is fluoro only when the other is hydrogen or fluoro;

wherein R$_7$ is (1) —(CH$_2$)$_m$—CH$_3$, wherein m is an integer from one to 5, inclusive;
(2) phenoxy;
(3) phenoxy substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
(4) phenyl;
(5) phenyl substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or
(7) phenylmethyl, phenylethyl, or phenylpropyl substituted by one, two or three chloro, fluoro, trifluoromethyl, alkyl of one to 3 carbon atoms, inclusive, or alkoxy of one to 3 carbon atoms, inclusive, or alkoxy of one to 3 carbon atoms, inclusive, with the proviso that not more than two substituents are other than alkyl; with the proviso that R$_7$ is phenoxy or substituted phenoxy, only when R$_3$ and R$_4$ are hydrogen or methyl, being the same or different;

wherein R$_1$ is (1) hydrogen;
(2) alkyl of one to 12 carbon atoms, inclusive;
(3) cycloalkyl of 3 to 10 carbon atoms, inclusive;
(4) aralkyl or 7 to 12 carbon atoms, inclusive;
(5) phenyl;
(6) phenyl substituted with one, 2 or 3 chloro or alkyl of one to 3 carbon atoms;
(7) phenyl substituted in the para position by
 (a) —NH—CO—R$_{25}$,
 (b) —CO—R$_{26}$,
 (c) —O—CO—R$_{27}$, or
 (d) —CH=N—NH—CO—NH$_2$, wherein R$_{25}$ is methyl, phenyl, acetamidophenyl, benzamidophenyl, or —NH$_2$; R$_{26}$ is hydroxy, methyl, phenyl, —NH$_2$, or methoxy; and R$_{27}$ is phenyl or acetamidophenyl, inclusive, or a pharmacologically acceptable salt thereof when R$_1$ is hydrogen.

The novel prostaglandin analogs prepared from the above intermediates are useful for a variety of prostacyclin-like pharmacological purposes, particularly and especially as inhibitors of platelet aggregation in vivo and in vitro. Thus, these prostacyclin analogs are useful for a variety of pharmacological and therapeutical purposes, e.g., as antithrombotic agents.

BACKGROUND OF THE INVENTION

This invention relates to novel structural and pharmacological analogs of prostacyclin (PGI$_2$), 5,6-dihydroprostacyclin (PGI$_1$), and 5,9α-epoxy-9-deoxy-PGF$_1$. In particular, the present invention relates to prostacyclin-type compounds wherein the alkylene chain between C-5 and C-2 is replaced by inter-o-phenylene and the epoxy oxygen is bonded to the C-5 position.

Prostacyclin is an endogenously produced compound in mammalian species, being structurally and biosynthetically related to the prostaglandins (PG's). In particular, prostacyclin exhibits the structure and carbon atom numbering of formula I.

5,6-Dihydroprostacyclin exhibits the structure and carbon atom numbering of formula II. Similarly formula III provides the structure and carbon atom numbering of 5,9α-epoxy-9-deoxy-PGF$_{1α}$.

As is apparent from inspection of formulas I, II, and III, prostacyclin, 5,6-dihydroprostacyclin (i.e., PGI$_1$), and 5,9α-epoxy-9-deoxy-PGF$_{1α}$ bear a structural relationship to PGF$_{2α}$, which exhibits the structure and carbon atom numbering of formula IV.

As is apparent by reference to formula IV, prostacyclin and 5,6-dihydroprostacyclin may be trivially named as derivatives of PGF-type compounds. Accordingly, prostacyclin is trivially named 6,9α-epoxy-9-deoxy-(5Z)-5,6-didehydro-PGF$_1$. For description of the geometric stereoisomerism employed above, see Blackwood et al., Journal of the American Chemical Society 90, 509 (1968). Further, for a description of prostacyclin and its structural identification, see Johnson, et al., Prostaglandins 12, 916 (1976).

For convenience, the novel prostacyclin analogs described herein will be referred to by the trivial artrecognized system of nomenclature described by N. A. Nelson, Med. Chem. 19:911 (1974) and Johnson, R. A., Prostaglandins 15:737 (1978). Accordingly, all of the novel prostacyclin derivatives herein will be named as 9-deoxy-PGF$_1$-type compounds or alternatively as PGI$_1$ or PGI$_2$ derivatives.

In the formulas referred to above, as well as in formulas hereinafter, broken line attachments to any ring indicate substituents in "alpha" ($\alpha$) configuration, i.e., below the plane of such ring. Heavy solid line attachments to any ring indicate substituents in "beta" ($\beta$) configuration, i.e., above the plane of such ring. The use of wavy lines herein will represent attachment of substituents in either the alpha or beta configuration or attachment in a mixture of alpha and beta configurations.

The side-chain hydroxy at C-15 in the above formulas is in S or R configuration, as determined by the Cahn-Ingold-Prelog sequence rules. See J. Chem. Ed. 41:16 (1964). See also Nature 212, 38 (1966) for discussion of the stereochemistry of the prostaglandins, which discussion applies to the novel prostacyclin analogs herein. Further, the carboxy-terminated side chain is attached to the heterocyclic ring of PGI$_1$ in either the alpha or beta configuration which by the above convention represents the (6R) or (6S) configuration, respectively. Expressions such as C-5, C-15, and the like, refer to the carbon atom in the prostaglandin or prostacyclin analog which is in the position corresponding to the position of the same number in PGF$_{2\alpha}$ or prostacyclin, as enumerated above.

Molecules of 5,9$\alpha$-epoxy-9-deoxy-PGF$_{1\alpha}$, PGI$_\alpha$, PGI$_\beta$, and the novel, asymmetric prostacyclin analogs each have several centers of asymmetry, and can exist in racemic (optically inactive) form and in either of the two enantiomeric (optically active) forms, i.e., the dextrorotatory and levorotatory forms. As drawn, the formula for PGI$_2$ corresponds to that endogenously produced in mammalian tissues. In particular, refer to the stereoconfiguration at C-8 (alpha), C-9 (alpha), C-11 (alpha), and C-12 (beta) of endogenously-produced prostacyclin.

For convenience hereinafter, use of the term prostaglandin ("PG") or prostacyclin ("PGI$_2$") will mean the optically active form of that prostaglandin or prostacyclin thereby referred to with the same absolute configuration of PGF$_{2\alpha}$, obtained from mammalian tissues.

The term "prostaglandin-type" or "prostacyclin-type" (PG-type or PGI-type) product, as used herein, refers to any monocyclic or bicyclic cyclopentane derivative herein which is useful for at least one of the same pharmacological purposes as the prostaglandin or prostacyclin, respectively.

The formulas as drawn herein, which depict a prostaglandin-type or prostacyclin-type product or an intermediate useful in their respective preparations, each represent the particular stereoisomer of the prostaglandin-type or prostacyclin-type product which is of the same relative stereochemical configuration as a corresponding prostaglandin or prostacyclin obtained from mammalian tissues, or the particular stereoisomer of the prostaglandin-type or prostacyclin-type products.

The term "prostaglandin analog" or "prostacyclin analog", as used herein, represents that stereoisomer of a prostaglandin- or prostacyclin-type product which is of the same relative stereochemical configuration as prostaglandins or prostacyclins obtained from mammalian tissues or a mixture comprising that stereoisomer and the enantiomer thereof. In particular, where a formula is used to depict a prostaglandin- or prostacyclin-type product herein, the term "prostaglandin analog" or "prostacyclin analog" refers to that compound of that formula or a mixture comprising that compound and the enantiomer thereof.

Numerous therapeutic indications for prostacyclin have been established, based on its vasoactive and platelet antiaggregatory activities: (a) platelet preservation in vitro; (b) platelet preservation in hemodialysis; (c) maintenance of platelet numbers and function and prevention of deposition or aggregation during surgery involving extracorporeal circulation; (d) prevention of CNS transient ischemic attacks or stroke or improvement of cerebral blood flow; (e) prevention or treatment of angina pectoris or myocardial infarction; (f) prevention of sudden cardiac death due to ventricular fibrillation; (g) prevention of postoperative venous thrombosis and thromboembolism; (h) pretransplantation perfusion of organs; (i) maintenance of patency in transplant or by-pass vessels; (j) prevention of deposits which could impair function or artificial heart valves; (k) treatment of microangiopathic hemolytic anemia; (l) treatment of peripheral vascular disease; (m) treatment of pulmonary hypertension; and (n) treatment of systemic hypertension.

PRIOR ART

Interphenylene analogs of the prostaglandins are known to be useful for the induction of prostaglandin-like pharmacological effects. Such compounds are described in U.S. Pat. No. 4,078,083, issued Mar. 7, 1978; U.S. Pat. No. 4,020,097, issued Apr. 26, 1977; and U.S. Pat. No. 3,928,418, issued Dec. 23, 1975.

SUMMARY OF THE INVENTION

The present specification particularly provides:
a prostacyclin analog of formula V or VI; and
a prostacyclin intermediate of formula VII, VIII, or IX,
wherein $Z_2$ is cis—CH=CH— or —CH$_2$CH$_2$—;
wherein $R_{28}$ is —OR$_{10}$, —CH$_2$OR$_{10}$, hydroxy, hydroxymethyl, or hydrogen, wherein $R_{10}$ is a blocking group;
wherein $R_8$ is hydrogen, hydroxy, or hydroxymethyl;
wherein $Y_1$ is
(1) trans—CH=CH—,
(2) cis—CH=CH—,
(3) —CH$_2$CH$_2$—, or
(4) —CH=C—,
wherein $M_1$ is $\alpha$-R$_5$:$\beta$-OH or $\alpha$-OH:$\beta$-R$_5$, wherein $R_5$ is hydrogen or alkyl with one to 4 carbon atoms, inclusive,
wherein $M_8$ is $\alpha$-R$_5$:$\beta$-OR$_{10}$ or $\alpha$-OR$_{10}$:$\beta$-R$_5$, wherein $R_5$ and $R_{10}$ are as defined above, or
$\alpha$-R$_5$:$\beta$-OH or $\alpha$-OH:$\beta$-R$_5$, wherein $R_5$ is as defined above;
wherein $L_1$ is $\alpha$-R$_3$:$\beta$-R$_4$, $\alpha$-R$_4$:$\beta$-R$_3$, or a mixture of $\alpha$-R$_3$:$\beta$-R$_4$ and $\alpha$-R$_4$:$\beta$-R$_3$, wherein $R_3$ and $R_4$ are hydrogen, methyl, or fluoro, being the same or different, with the proviso that one of $R_3$ and $R_4$ is fluoro only when the other is hydrogen or fluoro;
wherein $R_7$ is
(1) —(CH$_2$)$_m$—CH$_3$, wherein m is an integer from one to 5, inclusive;
(2) phenoxy;
(3) phenoxy substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
(4) phenyl;
(5) phenyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or
(7) phenylmethyl, phenylethyl, or phenylpropyl substituted by one, two or three chloro, fluoro, trifluoromethyl, alkyl of one to 3 carbon atoms, inclusive, or alkoxy of one to 3 carbon atoms, inclusive, with the proviso that not more than two substituents are other than alkyl; with the proviso that $R_7$ is phenoxy or substituted phenoxy, only when $R_3$ and $R_4$ are hydrogen or methyl, being the same or different;
wherein $X_1$ is
(1) —COOR$_1$, wherein $R_1$ is
(a) hydrogen;
(b) alkyl of one to 12 carbon atoms, inclusive;
(c) cycloalkyl of 3 to 10 carbon atoms, inclusive;
(d) aralkyl of 7 to 12 carbon atoms, inclusive;
(e) phenyl;
(f) phenyl substituted with one, two, or three chloro or alkyl of one to 3 carbon atoms;
(g) phenyl substituted in the para position by
  (i) —NH—CO—R$_{25}$
  (ii) —CO—R$_{26}$
  (iii) —O—CO—R$_{27}$
  (iv) —CH=N—NH—CO—NH$_2$
wherein $R_{25}$ is methyl, phenyl, acetamidophenyl, benzamidophenyl, or —NH$_2$; $R_{26}$ is hydroxy, methyl, phenyl, —NH$_2$, or methoxy; and $R_{27}$ is phenyl or acetamidophenyl; inclusive, or a pharmacologically acceptable cation; or
(2) —COL$_4$, wherein L$_4$ is
(a) amino of the formula —NR$_{21}$R$_{22}$, wherein $R_{21}$ and $R_{22}$ are
  (i) hydrogen;
  (ii) alkyl or one to 12 carbon atoms, inclusive;
  (iii) cycloalkyl of 3 to 10 carbon atoms, inclusive;
  (iv) aralkyl of 7 to 12 carbon atoms, inclusive;
  (v) phenyl;
  (vi) phenyl substituted with one, 2, or 3 chloro, alkyl of one to three carbon atoms, inclusive, hydroxy, carboxy, alkoxycarbonyl of one to 4 carbon atoms, inclusive, or nitro;
  (vii) carboxyalkyl of 2 to 5 carbon atoms, inclusive;
  (viii) carbamoylalkyl of 2 to 5 carbon atoms, inclusive;
  (ix) cyanoalkyl of 2 to 5 carbon atoms, inclusive;
  (x) acetylalkyl of 3 to 6 carbon atoms, inclusive;
  (xi) benzoylalkyl of 7 to 11 carbon atoms, inclusive;
  (xii) benzoylalkyl substitued by one, 2, or 3 chloro, alkyl of one to 3 carbon atoms, inclusive, hydroxy, alkoxy of one to 3 carbon atoms, inclusive, carboxy, alkoxycarbonyl of one to 4 carbon atoms, inclusive, or nitro;
  (xiii) pyridyl;
  (xiv) pyridyl substituted by one, 2, or 3 chloro, alkyl of one to 3 carbon atoms, inclusive, or alkoxy of one to 3 carbon atoms, inclusive;
  (xv) pyridylalkyl of 6 to 9 carbon atoms, inclusive;
  (xvi) pyridylalkyl substituted by one, 2, or 3 chloro, alkyl of one to 3 carbon atoms, inclusive, hydroxy or alkoxy of one to 3 carbon atoms, inclusive;
  (xvii) hydroxyalkyl of one to 4 carbon atoms, inclusive;
  (xviii) dihydroxyalkyl of one to 4 carbon atoms, or
  (xix) trihydroxyalkyl of one to 4 carbon atoms;
with the further proviso that not more than one of $R_{21}$ and $R_{22}$ is other than hydrogen or alkyl;
(b) cycloamino selected from the group consisting of
  (i) pyrrolidino,
  (ii) piperidino,
  (iii) morpholino,
  (iv) piperazino,
  (v) hexamethyleneimino,
  (vi) pyrrolino,
  (vii) 3,4-didehydropiperidinyl, or
  (viii) pyrrolidino, piperidino, morpholino, piperazino, hexamethyleneimino, pyrrolino, or 3,4-didehydropiperidinyl substituted by one or two alkyl of one to 12 carbon atoms, inclusive;
(c) carbonylamino of the formula —NR$_{23}$COR$_{21}$, wherein $R_{23}$ is hydrogen or alkyl of one to 4 carbon atoms and $R_{21}$ is other than hydrogen, but otherwise as defined above; or
(d) sulfonylamino of the formula —NR$_{23}$SO$_2$R$_{21}$, wherein $R_{21}$ and $R_{23}$ are as defined in (c);

With regard to the divalent substituents described above (e.g., L$_1$ and M$_1$), these divalent radicals are defined as α-R$_i$:β-R$_j$, wherein R$_i$ represents the substituent of the divalent moiety in the alpha configuration with respect to the plane of the ring and R$_j$ represents the substituent of the divalent moiety in the beta configuration with respect to the plane of the ring. Accordingly, when M$_1$ is defined as α-OH:β-R$_5$, the hydroxy of the M$_1$ moiety is in the alpha configuration, i.e., as in PGF$_2$ above, and the R$_5$ substituent is in the beta configuration. Not all carbon atoms to which such divalent moieties are attached represent asymmetric centers. For example when both valence bonds are to hydrogen (e.g., L$_1$ is α-H:β-H), then no asymmetric center is present.

The novel prostaglandin and prostacyclin analogs herein are all named as 2,5-inter-o-phenylene-3,4-dinor-PG compounds. Formula VI compounds are further named as 5,9α-epoxy-9-deoxy- or 5,9α-epoxy-9-deoxy-6,7-didehydro-PG compounds, depending on whether Z$_2$ is —CH$_2$CH$_2$—or cis—CH=CH—, respectively. Formula VI and formula VIII compounds are further named as 6β-PGI$_1$ compounds in view of their configuration at C-6.

The novel prostaglandin and prostacyclin analogs herein wherein R$_8$ is hydrogen or hydroxymethyl are respectively referred to as 11-deoxy-PG-type or 11-deoxy-11-hydroxymethyl-PG-type compounds. Additionally, when R$_1$ is cis—CH=CH—, —CH$_2$CH$_2$—, or —C≡C—, the novel compounds thereby referred to are named as 13-cis-PG-type, 13,14-dihydro-PG-type, or 13,14-didehydro-PG-type compounds, respectively.

Compounds herein wherein M$_1$ is α-OH:β-R$_5$ or α-R$_5$:β-OH and R$_5$ is alkyl are referred to as 15-alkyl-PG-type compounds.

With the exception of the 13-cis-PG-type compounds described above, all the above compounds exhibiting a hydroxy or alkoxy moiety in the beta configuration at C-15 are additionally referred to as 15-epi-PG-type compounds. For the 13-cis-PG-type compounds herein, only compounds exhibiting the hydroxy or alkoxy moiety in the alpha configuration at C-15 are referred to as 15-epi-PG-type compounds. The rationale for this system of nomenclature with respect to the natural and epimeric configurations at C-15 is described in U.S. Pat. No. 4,016,184, issued Apr. 5, 1977.

When $R_7$ is $-(CH_2)_m-CH_3$, wherein m is as defined above, the novel compounds herein are named as 19,20-dinor-PG-type, 20-nor-PG-type, 20-methyl-PG-type or 20-ethyl-PG-type compounds when m is one, 2, 4, or 5, respectively.

When $R_7$ is cis-$CH=CH-CH_2-CH_3-$, the novel compounds herein are named as PG$_3$ or cis-17,18-didehydro-PG compounds.

When $R_7$ is phenyl and neither $R_3$ or $R_4$ is methyl, the compounds so described are named as "16-phenyl-17,18,19,20-tetranor" compounds, when s is zero. When $R_7$ is substituted phenyl, the corresponding compounds are named as "16-(substituted phenyl)17,18,19,20-tetranor" compounds. When one and only one of $R_3$ and $R_4$ is methyl or both $R_3$ and $R_4$ are methyl, then the corresponding compounds wherein $R_7$ is as defined in this paragraph are named as "16-phenyl or 16-(substituted phenyl)-18,19,20-trinor" compounds or "16-methyl-16phenyl- or 16-(substituted phenyl)-18,19,20-trinor" compounds, respectively.

When $R_7$ is phenylmethyl, the compounds so described are named as "17-phenyl-18,19,20-trinor" compounds. When $R_7$ is substituted phenylmethyl the corresponding compounds are named as "17-(substituted phenyl)-18,19,20-trinor" compounds.

When $R_7$ is phenylethyl the compounds so described as named as "18-phenyl-19,20-dinor" compounds, when s is 0. When s is one, 2, or 3, the corresponding compounds are named as "18-(substituted phenyl)-19,20-dinor" compounds.

When $R_7$ is phenylpropyl, the compounds so described are named as "19-phenyl-20-nor" compounds. When $R_7$ is substituted phenylpropyl the corresponding compounds are named as "19-(substituted phenyl)-20-nor" compounds.

When $R_7$ is phenoxy and neither $R_3$ nor $R_4$ is methyl, the compounds so described are named as "16-phenoxy-17,18,19,20-tetranor" compounds. When $R_7$ is substituted phenoxy the corresponding compounds are named as "16-(substituted phenoxy)-17,18,19,20-tetranor" compounds. When one and only one of $R_3$ and $R_4$ is methyl or both $R_3$ and $R_4$ are methyl, then the corresponding compounds wherein $R_7$ is as defined in this paragraph are named as "16-phenoxy- or 16-(substituted phenoxy)-18,19,20-trinor" compounds or "16-methyl-16-phenoxy- or 16-(substituted phenoxy)-18,19,20-trinor" compounds, respectively.

When at least one of $R_3$ and $R_4$ is not hydrogen then (except for the 16-phenoxy or 16-phenyl compounds discussed above) there are described the "16-methyl" (one and only one of $R_3$ and $R_4$ is methyl), "16,16-dimethyl" ($R_3$ and $R_4$ are both methyl), "16-fluoro" (one and only one of $R_3$ and $R_4$ is fluoro), "16,16-difluoro" ($R_3$ and $R_4$ are both fluoro) compounds. For those compounds wherein $R_3$ and $R_4$ are different, the prostaglandin analogs so represented contain an asymmetric carbon atom at C-16. Accordingly, two epimeric configurations are possible: "(16S)" and "(16R)". Further, there is described by this invention the C-16 epimeric mixture: "(16RS)".

Examples of novel amides herein (i.e., $X_1$ is $-COL_4$) include the following:

(1) Amides within the scope of alkylamino groups of the formula $-NR_{21}R_{22}$ are methylamide, ethylamide, n-propylamide, n-butylamide, n-pentylamide, n-hexylamide, n-heptylamide, n-octylamide, n-nonylamide, n-decylamide, n-undecylamide, and n-dodecylamide, and isomeric forms thereof. Further examples are dimethylamide, diethylamide, di-n-propylamide, di-n-butylamide, methylethylamide, methylpropylamide, methylbutylamide, ethylpropylamide, ethylbutylamide, and propylbutylamide. Amides within the scope of cycloalkylamino are cyclopropylamide, cyclobutylamide, cyclopentylamide, 2,3-dimethylcyclopentylamide, 2,2-dimethylcyclopentylamide, 2-methylcyclopentylamide, 3-tert-butylcyclopentylamide, cyclohexylamide, 4-tert-butylcyclohexylamide, 3-isopropylcyclohexyl amide, 2,2-dimethylcyclohexylamide, cycloheptylamide, cyclooctylamide, cyclononylamide, cyclodecylamide, N-methyl-N-cyclobutylamide, N-methyl-N-cyclopentylamide, N-methyl-N-cyclohexylamide, N-ethyl-N-cyclopentylamide, and N-ethyl-N-cyclohexylamide. Amides within the scope of aralkylamino are benzylamide, 2-phenylethylamide, 2-phenylethylamide, and N-methyl-N-benzylamide. Amides within the scope of substituted phenylamido are p-chloroanilide, m-chloroanilide, 2,4-dichloroanilide, 2,4,6-trichloroanilide, m-nitroanilide, p-nitroanilide, p-methoxyanilide, 3,4-dimethoxyanilide, 3,4,5-trimethoxyanilide, p-hydroxymethylanilide, p-methylanilide, m-methylanilide, p-ethylanilide, t-butylanilide, p-carboxyanilide, p-methoxycarbonylanilide, o-carboxyanilide and o-hydroxyanilide. Amides within the scope of carboxyalkylamino are carboxymethylamide, carboxyethylamide, carboxypropylamide, and carboxybutylamide. Amides within the scope of carbamoylalkylamino are carbamoylmethylamide, carbamoylethylamide, carbamoylpropylamide, and carbamoylbutylamide. Amides within the scope of cyanoalkylamino are cyanomethylamide, cyanoethylamide, cyanopropylamide, and cyanobutylamide. Amides within the scope of acetylalkylamino are acetylmethylamide, acetylethylamide, acetylpropylamide, and acetylbutylamide. Amides within the scope of benzoylalkylamino are benzoylmethylamide, benzoylethylamide, benzoylpropylamide, and benzoylbutylamide. Amides within the scope of substituted benzoylalkylamino are p-chlorobenzoylmethylamide, m-chlorobenzoylmethylamide, 2,4-dichlorobenzoylmethylamide, 2,4,6-trichlorobenzoylmethylamide, m-nitrobenzoylmethylamide, p-nitrobenzoylmethylamide, p-methoxybenzoylmethylamide, 2,4-dimethoxybenzoylmethylamide, 3,4,5-trimethoxybenzoylmethylamide, p-hydroxymethylbenzoylmethylamide, p-methylbenzoylmethylamide, m-methylbenzoylmethylamide, p-ethylbenzoylmethylamide, t-butylbenzoylmethylamide, p-carboxybenzoylmethylamide, m-methoxycarbonylbenzoylmethylamide, o-carboxybenzoylmethylamide, o-hydroxybenzoylmethylamide, p-chlorobenzoylethylamide, m-chlorobenzoylethylamide, 2,4-dichlorobenzoylethylamide, 2,4,6-trichlorobenzoylethylamide, m-nitrobenzoylethylamide, p-nitrobenzoylethylamide, p-methoxybenzoylethylamide, p-methoxybenzoylethylamide, 2,4-dimethoxybenzoylethylamide, 3,4,5-trimethoxybenzoylethylamide, p-hydroxymethylbenzoylethylamide, p-methylbenzoylethylamide, m-methylbenzoylethylamide, p-ethylbenzoylethylamide, t-butylbenzoylethylamide, p-carboxybenzoylethylamide, m-methoxycarbonylbenzoylethylamide, o-carboxybenzoylethylamide, o-hydroxybenzoylethylamide, p-chlorobenzoylpropylamide, m-chlorobenzoylpropylamide, 2,4-dichlorobenzoylpropylamide, 2,4,6-trichlorobenzoylpropylamide, m-nitrobenzoylpropylamide, p-nitrobenzoylpropylamide, p-methoxybenzoylpropylamide, 2,4-dimethoxybenzoylpropylamide, 3,4,5-trimethoxybenzoylpropylamide, p-hydroxymethylbenzoylpropylamide, p-methylbenzoylpropylamide, m-methylbenzoylpropylamide, p-ethylbenzoylpropylamide, t-butylbenzoylpropylamide, p-carboxybenzoylpropylamide, m-methoxycarbonylbenzoylpropylamide, o-carboxybenzoylpropylamide, o-hydroxybenzoylpropylamide, p-chlorobenzoylbutylamide, m-chlorobenzoylbutylamide, 2,4-dichlorobenzoylbutylamide, 2,4,6-trichlorobenzoylbutylamide, m-nitrobenzoylmethylamide, p-nitrobenzoylbutylamide, p-methoxybenzoylbutylamide, 2,4-dimethoxybenzoylbutylamide, 3,4,5-trimethoxybenzoylbutylamide, p-hydroxymethylbenzoylbutylamide, p-methylbenzoylbutylamide, m-methylbenzoylbutylamide, p-ethylbenzoylbutylamide, m-methylbenzoylbutylamide, p-ethylbenzoylbutylamide, t-butylbenzoylbutylamide, p-carboxybenzoylbutylamide, m-methoxycarbonaylbenzoylbutylamide, o-carboxybenzoylbutylamide, o-hydroxybenzoylmethylamide. Amides within the scope of pyridylamino are α-pyridylamide, β-pyridylamide, and γ-pyridylamide. Amides within the scope of substituted pyridylamino are 4-methyl-α-pyridylamide, 4-methyl-β-pyridylamide, 4-chloro-α-pyridylamide, and 4-chloro-β-pyridylamide. Amides within the scope of pyridylalkylamino are α-pyridylmethylamide, β-pyridylmethylamide, γ-pyridylmethylamide, α-pyridylethylamide, β-pyridylethylamide, γ-pyridylethylamide, α-pyridylpropylamide, β-pyridylpropylamide, γ-pyridylpropylamide, α-pyridylbutylamide, β-pyridylbutylamide, and γ-pyridylbutylamide. Amides within the scope of substituted pyridylalkylamido are 4-methyl-α-pyridylmethylamide, 4-methyl-β-pyridylmethylamide, 4-chloro-α-pyridylmethylamide, 4-chloro-β-pyridylmethylamide, 4-methyl-α-pyridylpropylamide, 4-methyl-β-pyridylpropylamide, 4-chloro-α-pyridylpropylamide, 4-chloro-β-pyridylpropylamide, 4-methyl-α-pyridylbutylamide, 4-methyl-β-pyridylbutylamide, 4-chloro-α-pyridylbutylamide, 4-chloro-β-pyridylbutylamide, 4-methyl-β-pyridylbutylamide. Amides within the scope of hydroxyalkylamino are hydroxymethylamide, α-hydroxyethylamide, β-hydroxyethylamide, α-hydroxypropylamide, β-hydroxypropylamide, γ-hydroxypropylamide, 1-(hydroxymethyl)ethylamide, 1-(hydroxymethyl)propylamide, (2-hydroxymethyl)propylamide, and α,α-dimethyl-β-hydroxyethylamide. Amides within the scope of dihydroxyalkylamino are dihydroxymethylamide, α,α-dihydroxyethylamide, α,β-dihydroxyethylamide, β,β-dihydroxyethylamide, α,α-dihydroxypropylamide, α,β-dihydroxypropylamide, α,γ-dihydroxypropylamide, β,β-dihydroxypropylamide, β,γ-dihydroxypropylamide, γ,γ-dihydroxypropylamide, 1-(hydroxymethyl)-2-hydroxymethylamide, 1-(hydroxymethyl)-1-hydroxyethylamide, α,α-dihydroxybutylamide, α,β-dihydroxybutylamide, α,γ-dihydroxybutylamide, α,δ-dihydroxybutylamide, β,β-dihydroxybutylamide, β,γ-dihydroxybutylamide, β,δ-dihydroxybutylamide, γ,γ-dihydroxybutylamide, γ,δ-didihydroxybutylamide, δ,δ-dihydroxybutylamide, and 1,1-bis(hydroxymethyl)ethylamide. Amides within the scope of trihydroxyalkylamino are tris(hydroxymethyl)methylamide and 1,3-dihydroxy-2-hydroxymethylpropylamide.

(2) Amides within the scope of cycloamino groups described above are pyrrolidylamide, piperidylamide, morpholinylamide, hexamethyleneiminylamide, piperazinylamide, pyrrolinylamide, and 3,4-didehydropiperidinylamide.

(3) Amides within the scope of carbonylamino of the formula —$NR_{23}COR_{21}$ are methylcarbonylamide, ethylcarbonylamide, phenylcarbonylamide, and benzylcarbonylamide.

(4) Amides within the scope of sulfonylamino of the formula —$NR_{23}SO_2R_{21}$ are methylsulfonylamide, ethylsulfonylamide, phenylsulfonylamide, p-tolylsulfonylamide, benzylsulfonylamide.

Examples of alkyl of one to 12 carbon atoms, inclusive, are methyl, ethyl, propyl, butyl, pentyl, hexyl, heptyl, octyl, nonyl, decyl, undecyl, dodecyl, and isomeric forms thereof.

Examples of cycloalkyl of 3 to 10 carbon atoms, inclusive, which includes alkyl-substituted cycloalkyl, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclononyl, and cyclodecyl.

Examples of aralkyl of 7 to 12 carbon atoms, inclusive, are benzyl, 2-phenethyl, 1-phenylethyl, 2-phenylpropyl, 4-phenylbutyl, 3-phenylbutyl, 2-(1-napthylethyl), and 1-(2-napthylmethyl).

Examples of phenyl substituted by one to 3 chloro or alkyl of one to 4 carbon atoms, inclusive, are p-chlorophenyl, m-chlorophenyl, 2,4-dichlorophenyl, 2,4,6-trichlorophenyl, p-tolyl, m-tolyl, o-tolyl, p-ethylphenyl, p-tertbutylphenyl, 2,5-dimethylphenyl, 4-chloro-2-methylphenyl, and 2,4-dichloro-3-methylphenyl.

Examples of substituted phenoxy, phenylmethyl, phenylethyl, or phenylpropyl of the $R_7$ moiety are (o-, m-, or p-)tolyl, (o-, m-, or p-)ethylphenyl, 2-ethyltolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,5-, 2,3,6-, or 2,4,5-)trimethylphenyl, (o-, m-, or p-)fluorophenyl, 2-fluoro-(o-, m-, or p-)tolyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-,4-,5-, or 6-)chloro-o-tolyl, 4-chloro-2-propylphenyl, 2-isopropyl-4-chlorophenyl, 4-chloro-3,5-xylyl, (2,3-, 2,4-, 2,5-, 2,6-, 3,4-, or 3,5-)dichlorophenyl, 4-chloro-3-fluorophenyl, (3- or 4-)chloro-2-fluorophenyl, (o-, m-, or p-)trifluoromethylphenyl, (o-, m-, or p-)methoxyphenyl, (o-, m-, or p-)ethoxyphenyl, (4- or 5-)chloro-2-methoxyphenyl, 2,4-dichloro-(4- or 6-)methylphenyl, (o-, m-, or p-)tolyloxy, (o-, m-, or p-)ethylphenyloxy, 2-ethyltolyloxy, 4-ethyl-o-tolyloxy, 5-ethyl-m-tolyloxy, (o-, m-, or p-) propylphenoxy, 2-propyl-(o-, m-, or p-)tolyloxy, 4-isopropyl-2,6-xylyloxy, 3-propyl-4-ethylphenyloxy, (2,3,4-, 2,3,5-, 2,3,6-, or 2,4,5-)trimethylphenoxy, (o-, m-, or p-)fluorophenoxy, 2-fluoro-(o-, m-, or p-)tolyloxy, 4-fluoro-2,5-xylyloxy, (2,4-, 2,5-, 2,6-, 3,4-, or 3,5-)difluorophenoxy, (o-, m-, or p-)chlorophenoxy, 2-chloro-p-tolyloxy, (3-, 4-, 5, or 6-)chloro-o-tolyloxy, 4-chloro-2-propylphenoxy, 2-isopropyl-4-chlorophenoxy, 4-chloro-3,5-xylyloxy, (2,3-, 2,4-, 2,5-, 2,6-, 3,4-, or 3,5-)dichlorophenyloxy, 4-chloro-3-fluorophenoxy, (3- or 4-)chloro-2-fluorophenoxy, (o-, m-, or p-)trifluoromethylphenoxy, (o-, m-, or p-)methoxyphenoxy, (o-, m-, or p-)-ethoxyphenoxy, (4- or 5-)chloro-2-methoxyphenoxy, 2,4-dichloro-(5- or 6-)methylphenoxy, (o-, m-, or p-)tolylmethyl, (o-, m-, or p-)ethylphenylmethyl, 2-ethyltolylmethyl, 4-ethyl-o-tolylmethyl, 5-ethyl-m-tolylmethyl, (o-, m-, or p-)propylphenylmethyl, 2-propyl-(o-, m-, or p-)tolyl-methyl, 4-isopropyl-2,6-xylylmethyl, 3-propyl-4-ethylphenylmethyl, (2,3,4-, 2,3,5-, 2,3,6-, or 2,4,5-)trimethylphenylmethyl, (o-, m-, or p-)fluorophenylmethyl, 2-fluoro-(o-, m-, or p-)tolylmethyl, 4-fluoro-2,5-xylylmethyl, (2,4-, 2,5-, 2,6-, 3,4-, or 3,5-)difluorophenyl, (o-, m-, or p-)chlorophenylmethyl, 2-chloro-p-tolylmethyl, (3-, 4-, 5-, or 6-)chloro-o-tolylmethyl, 4-chloro-2-propylphenylmethyl, 2-isopropyl-4-chlorophenylmethyl, 4-chloro-3,5-xylylmethyl, (2,3-, 2,4-, 2,5-, 2,6-, 3,4-, or 3,5-)dichlorophenylmethyl, 4-chloro-3-fluorophenylmethyl, (3- or 4-)chloro-2-fluorophenylmethyl, (o-, m-, or p-)trifluoromethylphenylmethyl, (o-, m-, or p-)methoxyphenylmethyl, (o-, m-, or p-)ethoxyphenylmethyl, (4- or 5-)chloro-2-methoxyphenylmethyl, and 2,4-dichloro-(4- or 6-)methoxyphenylmethyl.

The term "pharmacologically acceptable cation" refers to those pharmacologically acceptable salts of the prostaglandin- or prostacyclin-type carboxylic acids ($X_1$ is —COOH) described above which are conventionally employed with prostaglandins. In particular, such pharmacologically acceptable salts include pharmacologically acceptable metal cations, amine cations, and quarternary ammonium cations. Additionally basic amino acids such as arginine and lysine are employed. Further, certain amine cations such as THAM [tris(hydroxymethyl)aminomethyl] and adamantanamine as especially useful for the present purposes. Additionally, U.S. Pat. No. 4,016,184, issued Apr. 5, 1977 (particularly column 29), describes salts which are likewise preferred for the present purposes.

The novel prostaglandin and prostacyclin analogs disclosed herein produce certain prostacyclin-like pharmacological responses.

Accordingly, the novel prostaglandin and prostacyclin analogs disclosed herein are used as agents in the study, prevention, control, and treatment of diseases, and other undesirable physiological conditions, in mammals, particularly humans, valuable domestic animals, pets, zoological specimens, and laboratory animals (e.g., mice, rats, rabbits and monkeys). In particular, these compounds have useful application as smooth muscle stimulators, antihypertensive agents, antithrombotic agents, antiulcer agents, antiasthma agents, and antidermatosis agents, as indicated below.

(a) Smooth Muscle Stimulation

The novel prostaglandin and prostacyclin analogs herein are extremely potent in causing stimulation of smooth muscle, and are also highly active in potentiating other known smooth muscle stimulators, for example, oxytocic agents, e.g., oxytocin, and the various ergot alkaloids including derivatives and analogs thereof. Therefore, they are useful in place of or in combination with less than usual amounts of these known smooth muscle stimulators, for example, to relieve the symptoms of paralytic ileus, or to control or prevent atonic uterine bleeding after abortion or delivery, to aid in expulsion of the placenta, and during the puerperium. For the latter purpose the compound is administered by intravenous infusion immediately after abortion or delivery at a dose in the range about 0.01 to about 50 μg per kg of body weight per minute until the desired effect is obtained. Subsequent doses ar given by intravenous, subcutaneous, or intramuscular injection or infusion during puerperium in the range 0.01 to 2 mg per kg of body weight per day, the exact dose depending on the age, weight and condition of the patient or animal.

(b) Platelet Aggregation Inhibition

These novel prostaglandin and prostacyclin analogs are useful whenever it is desired to inhibit platelet aggregation, to reduce the adhesive character of platelets, or to remove or prevent the formation of thrombi in mammals, including man. For example, these compounds are useful in the treatment and prevention of myocardial infarcts, to treat and prevent post-operative thrombosis, to promote patency of vascular grafts following surgery, and to treat conditions such as atherosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range about 0.01 to about 10 mg per kg of body weight per day are used, the exact dose depending on the age, weight, and condition of the patient or animal, and on the frequency and route of administration.

The preferred dosage form for these compounds is oral, although other non-parenteral routes (e.g., buccal, rectal, sublingual) are likewise employed in preference to parenteral routes. Oral dosage forms are conventionally formulated (tablets, capsules, et cetera) and administered 2 to 4 times daily. Doses in the range of about 0.05 to 100 mg/kg of body weight per day are effective.

The addition of these compounds to whole blood provides in vitro applications such as storage of whole blood to be used in heart-lung machines. Additionally whole blood containing these compounds can be circulated through organs, e.g., heart and kidneys, which have been removed from a donor prior to transplant. They are also useful in preparing platelet rich concentrates for use in treating thrombocytopenia, chemotherapy, and radiation therapy. In vitro applications utilize a dose of 0.001–1.0 μg per ml of whole blood.

(c) Blood Pressure Reduction

The novel prostaglandin and prostacyclin analogs herein are useful as hypotensive agents to reduce blood pressure in mammals, including man. For this purpose, the compounds are administered by intravenous infusion at the rate about 0.01 to about 50 μg per kg of body weight per minute or in single or multiple doses of about 25 to 500 μg per kg of body weight total per day.

As for the antithrombotic application described above, these compounds are most preferably administered orally or by other convenient non-parenteral dosage form. In determining the appropriate oral dosage and frequency of administration, titration of dose in conjunction with other antihypertensive drugs being concomitantly administered is required. When used as the sole antihypertensive agent, determining the minimum effective dose required for adequate control of blood pressure is undertaken by initiating therapy at or near the threshold dose of patient or animal response.

Thereafter upward adjustment of the dosage, until full control is achieved or undesired side effects are observed, is undertaken. Accordingly threshold dosages of 0.01 to 1.0 mg per kg of body weight are employed.

(d) Gastric Secretion Reduction

These novel prostaglandin and prostacyclin analogs are also useful in mammals, including man and certain useful animals, e.g., dogs and pigs, to reduce and control gastric secretion, thereby to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range about 0.1 $\mu$g to about 20 $\mu$g per kg of body weight per minute, or in a total daily dose by injection or infusion in the range about 0.01 to about 10 mg per kg of body weight per day, the exact dose depending on the age, weight, and condition of the patient or animal, and on the frequency and route of administration.

Preferably, however, these novel compounds are administered orally or by other non-parenteral routes. As employed orally, one to 6 administrations daily in a dosage range of about 1.0 to 100 mg per kg of body weight per day is employed. Once healing of the ulcers has been accomplished the maintenance dosage required to prevent recurrence is adjusted downward so long as the patient or animal remains asymptomatic.

(e) NOSAC-Induced Lesion Inhibition

These novel prostaglandin and prostacyclin analogs herein are also useful in reducing the undesirable gastrointestinal effects resulting from systemic administration of anti-inflammatory prostaglandin synthetase inhibitors, and are useful for that purpose by concomitant administration of the prostaglandin derivative and the anti-inflammatory prostaglandin synthetase inhibitor. See Partridge, et al., U.S. Pat. No. 3,781,429, for a disclosure that the ulcerogenic effect induced by certain non-steroidal anti-inflammatory agents in rats is inhibited by concomitant oral administration of certain prostaglandins. Accordingly these novel prostaglandin and prostacyclin analogs herein are useful, for example, in reducing the undesirable gastrointestinal effects resulting from systemic administration of indomethacin, phenylbutazone, and aspirin. These are substances specifically mentioned in Partridge, et al. as nonsteroidal, anti-inflammatory agents. These are also known to be prostaglandin synthetase inhibitors.

The anti-inflammatory synthetase inhibitor, for example, indomethacin, aspirin, or phenylbutazone is administered in any of the ways known in the art to alleviate an inflammatory condition, for example, in any dosage regimen and by any of the known routes of systemic administration.

(f) Bronchodilation (Antiasthma)

These novel prostaglandin and prostacyclin analogs are also useful in the treatment of asthma. For example, these compounds are useful as bronchodilators or as inhibitors of mediator-induced bronchoconstriction, such as SRS-A, and histamine which are released from cells activated by an antigen-antibody complex. Thus, these compounds control spasm and facilitate breathing in conditions such as bronchial bronchitis, bronchiectasis, pneumonia and emphysema. For these purposes, these compounds are administered in a variety of dosage forms, e.g., orally in the form of tablets, capsules, or liquids; rectally in the form of suppositories, parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg per kg of body weight are used 1 to 4 times a day, the exact dose depending on the age, weight, and condition of the patient and on the frequency and route of administration. For the above use these prostaglandin and prostacyclin analogs can be combined advantageously with other anti-asthmatic agents, such as sympathomimetics (isoproterenol, phenylephrine, ephedrine, etc.); xanthine derivatives (theophylline and aminophylline); and corticosteroids (ACTH and prednisolone).

These compounds are effectively administered to human asthma patients by oral inhalation or by aerosol inhalation. For administration by the oral inhalation route with conventional nebulizers or by oxygen aerosolization it is convenient to provide the instant active ingredient in dilute solution, preferably at concentrations of about one part of medicament to form about 100 to 200 parts by weight of total solution. Entirely conventional additives may be employed to stabilize these solutions or to provide isotonic media, for example, sodium chloride, sodium citrate, citric acid, sodium bisulfite, and the like can be employed. For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethanol) together with a co-solvent, such as ethanol, flavoring materials and stabilizers. Instead of a co-solvent there can also be used a dispensing agent such as ethyl alcohol. Suitable means to employ the aerosol inhalation therapy technique are described fully in U.S. Pat. No. 3,868,691, for example.

(g) Dermatosis Reversal

These novel prostaglandin and prostacyclin analogs are useful for treating proliferating skin diseases of man and domesticated animals, incuding psoriasis, atopic dermatitis, non-specific dermatitis, primary irritant contact dermatitis, allergic contact dermatitis, basal and squamous cell carcinomas of the skin, lamellar ichthyosis, epidermolytic hyperkeratosis, premalignant sun-induced keratosis, non-malignant keratosis, acne, and seborrheic dermatitis in humans and atopic dermatitis and mange in domesticated animals. These compounds alleviate the symptoms of these proliferative skin diseases: psoriasis, For example, being alleviated when a scale-free psoriasis lesion is noticeably decreased in thickness and noticeably, but incompletely cleared, or completely cleared.

For these purposes, these compounds are applied topically as compositions including a suitable pharmaceutical carrier, for example as an ointment, lotion, paste, jelly, spray, or aerosol, using topical bases such as petrolatum, lanolin, polyethylene glycols, and alcohols. These compounds, as the active ingredients, constitute from about 0.1% to about 15% by weight of the composition, preferably from about 0.5% to about 2%. In addition to topical administration, injection may be employed, as intradermally, intra- or peri-lesionally, or subcutaneously, using appropriate sterile saline compositions.

Within the scope of the novel prostaglandin and prostacyclin analogs described above, certain compounds are preferred in that they exhibit increased potency, selectivity of action, or otherwise represent especially convenient and useful agents. Preferred are the formula V compounds, especially those wherein $Z_2$ is cis—CH=CH—.

With respect to the $Y_1$ moiety, preferred compounds are those wherein $Y_1$ is trans—CH=CH— or —CH$_2$CH$_2$—, the most especially preferred compounds being those wherein $Y_1$ is trans—CH=CH—. With respect to the $M_1$ moiety, preferred compounds are those wherein $M_1$ is $\alpha$-OH:$\beta$-$R_5$.

With respect to the $L_1$ moiety, those compounds wherein $R_3$ and $R_4$ are the same are preferred. Further preferred are those compounds herein wherein at least one of $R_3$, $R_4$, and $R_5$ is hydrogen. In the event $Y_1$ is cis—CH=CH— or —C≡C—, compounds wherein $R_3$, $R_4$, and $R_5$ are all hydrogen are preferred.

With respect to the integer m, it is preferred that m be 3. Among the compounds wherein $R_7$ is aromatic, the preferred compounds are the phenyl or phenylmethyl compounds either unsubstituted or substituted by one of chloro, fluoro, or trifluoromethyl.

With respect to the novel amides herein, preferred compounds are those wherein $R_{21}$ and $R_{22}$ are preferably hydrogen or alkyl of one to 8 carbon atoms, inclusive, being the same or different, preferably with the total number of carbon atoms in $R_{21}$ and $R_{22}$ being less than or equal to 8. More especially preferred are those amides wherein $R_{21}$ and $R_{22}$ are hydrogen or alkyl of one to 4 carbon atoms, inclusive, being the same or different, with the total number of carbon atoms in $R_{21}$ and $R_{22}$ being less than or equal to 4. Further $R_{23}$ is preferably hydrogen.

Of the various esters, methyl is most preferred with alkyl of one to 4 carbon atoms, para-substituted phenyl and alkylcarbonylphenyl being also preferred.

The chart herein describes the method by which the novel prostaglandin or prostacyclic analogs herein are prepared from known or readily synthesized starting materials.

With respect to this chart, $L_1$, $M_1$, $M_8$, $X_1$, $Y_1$, $R_7$, $R_8$, and $R_{28}$ are as defined above.

$R_{28}$ is —OR$_{10}$, —CH$_2$OR$_{10}$, or hydrogen, wherein $R_{10}$ is a blocking group as defined above. In particular $R_{10}$ is a readily acid hydrolyzable blocking group such as tetrahydrofuranyl or tetrahydropyranyl. For examples of blocking groups especially contemplated by the present invention see U.S. Pat. No. 4,016,184, issued Apr. 5, 1977. $R_{19}$ is —Si(G$_1$)$_3$, silyl groups, particularly those described in U.S. Pat. No. 4,016,184. For the purposes of the present invention stable silyl groups such as t-butyldimethylsilyl are especially contemplated.

$M_8$ is $\alpha$-$R_5$:$\beta$-OR$_{10}$ or $\alpha$-OR$_{10}$:$\beta$-$R_5$, wherein $R_5$ and $R_{10}$ are as defined above.

$Y_2$ is trans—CH=CH—, cis—CH=CH—, —CH$_2$CH$_2$—, or trans—CH=C(Hal), wherein Hal is chloro, bromo, or iodo.

With respect to Chart A a method is provided whereby the novel compounds of formula XXII-XXVIII are prepared.

The various formula XXI compounds employed as starting materials in the present synthesis are conveniently prepared from known or readily available starting materials. Formula XXI encompasses compounds deoxygenated at the latent C-11 (for preparing 11-deoxy-PGI$_1$-type compounds) or substituted at the latent C-11 by an hydroxymethyl in place of the hydroxy (for preparing 11-deoxy-11-hydroxymethyl-PGI$_1$-type compounds). These compounds are prepared by methods known in the art from the corresponding 11-deoxy- or 11-deoxy-11-hydroxymethyl-PG's.

The formula XXII compound is prepared from the formula XXI compound by a Wittig reaction, employing a triphenylphosphonium reagent of the formula Br—(Ph)$_3$P$^+$CH$_2$—(o—Ph)—CH$_2$—COOH, wherein Ph is phenyl and o-Ph is ortho-phenylene. When $Y_2$ is trans—CH=C(Hal)— the Wittig reaction is followed by dehydrohalogenation as described in U.S. Pat. No. 4,029,681.

The formula XXIII pharmacologically acceptable salts of the formula XXII carboxylic acids are then obtained by neutralization with a corresponding base. Conventional techniques of isolation and recovery of the salt are employed.

With respect to the novel formula XXIII PG-type amides ($X_1$ is —COL$_4$) and esters, especially p-substituted phenyl esters ($R_1$ is p-substituted phenyl), such compounds from the formula XXII acids are prepared as follows:

With regard to the preparation of the esters, especially p-substituted phenyl esters disclosed herein, such compounds are prepared by the method described in U.S. Pat. No. 3,890,372. Accordingly, by the preferred method described therein, the p-substituted phenyl ester is prepared first by forming a mixed anhydride, particularly following the procedures described below for preparing such anhydrides as the first step in the preparation of amino and cycloamino derivatives.

This PG-type anhydride is then reacted with a solution of the phenol corresponding to the p-substituted phenyl ester to be prepared. This reaction proceeds preferably in the presence of a tertiary amine such as pyridine. When the conversion is complete, the p-substituted phenyl ester has been recovered by conventional techniques.

Having prepared the PG-type carboxylic acids, the corresponding carboxyamides are then prepared by one of several amidation methods known in the prior art. See, for example, U.S. Pat. No. 3,981,868, issued Sept. 21, 1976, for a description of the preparation of the present amino and cycloamino derivatives of prostaglandin-type free acids and U.S. Pat. No. 3,954,741, describing the preparation of carbonylamino and sulfonylamino derivatives of prostaglandin-type free acids.

The preferred method by which the present amino and cycloamino derivatives of the novel prostacyclin-type free acids are prepared is, first by transformation of such free acids to corresponding mixed acid anhydrides. By this procedure, the prostaglandin-type free acid is first neutralized with an equivalent of an amine base, and thereafter reacted with a slight stoichiometric excess of a chloroformate corresponding to the mixed anhydride to be prepared.

The amine base preferred for neutralization is triethylamine, although other amines (e.g., pyridine, methyldiethylamine) are likewise employed. Further, a convenient, readily available chloroformate for use in the mixed anhydride production is isobutyl chloroformate.

The mixed anhydride formation proceeds by conventional methods and accordingly the PGF-type free acid is mixed with both the tertiary amine base and the chloroformate in a suitable solvent (e.g., aqueous tetrahydrofuran), allowing the reaction to proceed at $-10°$ to $20°$ C.

Thereafter, the mixed anhydride is converted to the corresponding amino or cycloamino derivative by reaction with the amine corresponding to the amide to be prepared. In the case where the simple amide (—NH$_2$) is to be prepared, the transformation proceeds by the addition of ammonia. Accordingly, the corresponding amine (or ammonia) is mixed with the mixed anhydride at or about −10° to +10° C., until the reaction is shown to be complete. For highly volatile amines, acid addition salts thereof (e.g., methylamine hydrochloride) are employed in place of the corresponding free base (e.g., methylamide).

Thereafter, the novel PGF-type amino or cycloamino derivative is recovered from the reaction mixture by conventional techniques.

The carbonylamino and sulfonylamino derivatives of the presently disclosed PG-type compounds are likewise prepared by known methods. See, for example, U.S. Pat. No. 3,954,741 for a description of the methods by which such derivatives are prepared. By this known method, the prostaglandin-type free acid is reacted with a carboxyacyl and sulfonyl isocyanate, corresponding to the carbonylamino or sulfonylamino derivative to be prepared.

By another, more preferred method the sulfonylamino derivatives of the present compounds are prepared by first generating the PG-type mixed anhydride, employing the method described above for the preparation of the amino and cycloamino derivatives. Thereafter, the sodium salt of the corresponding sulfonamide is reacted with the mixed anhydride and hexamethylphosphoramide. The pure PG-type sulfonylamino derivative is then obtained from the resulting reaction mixture by conventional techniques.

The sodium salt of the sulfonamide corresponding to the sulfonylamino derivatives to be prepared is generated by reacting the sulfonamide with alcoholic sodium methoxide. Thus, by a preferred method, methanolic sodium methoxide is reacted with an equal molar amount of the sulfonamide. The sulfonamide is then reacted, as described above, with the mixed anhydride, using about four equivalents of the sodium salt per equivalent of anhydride. Reaction temperatures at or about 0° C. are employed.

With regard to the phenacyl or substituted phenacyl esters herein, see U.S. Pat. No. 3,979,440 for a description of their preparations.

The formula XXIV and XXV compounds are prepared as a mixture from the formula XXIII compound by iodination and cyclization. Examples of such cyclization procedures are provided in Staninets and Schilof, Chemical Abstracts 64:21625H (1966). Iodination proceeds in an aqueous system containing iodide, potassium iodide, and an alkali carbonate or bicarbonate. Optionally iodination proceeds in organic solvent systems such as dichloromethane containing iodine in the presence of an alkali metal carbonate. While reaction temperature below about 25° C. are employed, most preferrably reaction temperatures about 0°–5° C. yield the desire product. When thin layer chromatographic analysis indicates the reaction is complete (e.g., 10–20 hr), the reaction mixture is quenched with addition of sodium sulfite and sodium carbonate, thereby yielding the desired product. Optionally to the method of Chart A, bromonation rather than iodination may be employed. Accordingly there is prepared a bromo compound corresponding to the formula XXIV iodo compound, which is used in subsequent reaction steps of Chart A. In undertaking such a bromonation agents such as N-bromosuccinimide or N-bromoacetamide are employed. See Fieser, et al., Reagents for Organic Synthesis, Vol. I, pages 74 and 78, and Vol. IV, page 51, John Wiley and Sons, New York, N.Y.

Thereafter the formula XXVI and XXVIII products are prepared from the mixture of formula XXIV and XXV compounds by reductive deiodination. Useful reagents for this purpose include tributyltin hydride, triphenyltinhydride, sodium borohydride and dimethylsulfoxide, in zinc and acetic acid. The especially preferred deiodination reagent is tributyltin freshly prepared from tributyltin chloride and a lithium aluminum hydride. The reaction proceeds in an organic solvent, preferably benzene, at 15°–35° C. Reaction mixtures are maintained until silica gel TLC analysis indicates the reaction is complete. Conventional separation techniques (e.g., column chromotography) yield pure formula XXVI or XXVIII products.

Also prepared from the formula XXV compound is the formula XXVII compound by dehydrohalogenation or dehydroiodination. Dehydroiodination reagents for this purpose are known in the art, for example, see Fieser, Reagents for Organic Synthesis, page 1308, John Wiley and Sons, New York, N.Y. (1966). Preferred dihydroiodinating reagents are tertiary amines, sodium or potassium superoxides, sodium or potassium carbonates, sodium or potassium hydroxides, sodium or potassium benzoates, sodium or potassium acetates, sodium or potassium trifluoroacetates, sodium or potassium bicarbonates, silver acetate or a tetraalkylammonium superoxide. Of the tertiary amines, 1,5-diazabicyclo[4.3.0]nonene-5 (DBN) and 1,5-diazabicyclo[5.4.0]undecene-5 (DBU).

For a description of the superoxides employed in this transformation see Johnson, R. A., et al., Org. Chem. 40:1680 (1975). Also, the large scale generation of superoxides is described in Dietz, et al., J. Chem. Soc. (B), 1970, pages 816–820.

Dehydroiodination is carried out in an organic medium, such as toluene, and is monitored by silica gel TLC to determine the completion of the reaction. Ordinarily reaction temperatures at about ambient temperature are employed, although somewhat higher temperatures (e.g., 40°–80° C.) are also useful in accelerating the reaction.

DESCRIPTION OF THE PREFERRED EMBODIMENTS

The invention can be more fully understood by the following exmaples and preparations.

All temperatures are in degrees centigrade.

DBN is 1,5-diazabicyclo[4.3.0]nonene-5.

DBU is 1,5-diazabicyclo[5.4.0]undecene-5.

IR (infrared) absorption spectra are recorded on a Perkin-Elmer Model 421 infrared spectrophotometer. Except when specified otherwise, undiluted (neat) samples are used.

UV (Ultraviolet) spectra are recorded on a Cary Model 15 spectrophotometer.

NMR (Nuclear Magnetic Resonance) spectra are recorded on a Varian A-60, A-60D, or T-60 spectrophotometer in deuterochloroform solutions with tetramethylsilane as an internal standard (downfield).

Mass spectra are recorded on a CEG model 110B double Focusing High Resolution Mass Spectrometer or an LKB Model 9000 Gas-Chromatograph-Mass Spectrometer. Trimethylsilyl derivatives are used, except where otherwise indicated.

"Brine", herein, refers to an aqueous saturated sodim chloride solution.

The A-IX solvent system used in thin layer chromatography is made up from ethyl acetate-acetic acid-2,2,4-trimethylpenantane-water (90:20:50:100) according to M. Hamber and B. Samuelsson, J. Biol. Chem. 241, 258 (1966).

Skellysolve-B (SSB) refers to mixed isomeric hexanes.

Silica gel chromatography, as used herein, is understood to include elution, collection of fractions and combination of those fractions shown by TLC (thin layer chromatography) to contain the pure product (i.e., free of starting material and impurities).

Melting point (MP) are determined on a Fisher-John or Thomas-Hoover melting point apparatus.

THF refers to tetrahydrofuran.

Specific Rotations, ($\alpha$), are determined for solutions of a compound in the specified solvent at ambient temperature with a Perkin-Elmer Model 141 Automatic Polarimeter.

EXAMPLE 1

A. o-[(carboxymethyl)benzyl]triphenylphosphonium bromide.

3-Isochromanone (30 g), Mann, F. G. and Stewart, F. H., Journal of the Chemical Society 2819 (1954) is added with swirling to 150 ml of hydrobromic acid (48%) at 80° C. The resulting mixture is then heated on a steam bath with occasional swirling for 10 min and thereafter poured into a mixture of crushed ice and water (750 g). The resulting mixture is then extracted with ethyl acetate and the ethyl acetate extracts washed with a mixture of water and brine (1:1) and dried over magnesium sulfate. Concentration under reduced pressure yields a residue of crude o-(bromomethyl)phenylacetic acid. (Crystallization of the crude product from methylene chloride yields a product with melting point 130°–131° C. and a C:H ration of 46.90:4.09). The crude o-(bromomethyl)phenylacetic acid, 400 ml of benzene and 38 g of triphenylphospine is stirred at 80° C. for 5 hr and cooled and filtered to yield 57 g of title product, melting point 248°–249° C. The C:H:Br:P ratio is 66.22:4.94:16.16:6.49.

B. 3,4-Dinor-2,5-inter-o-phenylene-PGF$_{2\alpha}$, 11,15-(bis(tetrahydropyranyl ether), methyl ester (formula XXII compound).

A mixture of 2.6 g of 57% sodium hydride in 100 ml of dry dimethylsulfoxide at 66°–70° C. is slowly stirred under a nitrogen atmosphere for one hr. The resulting solution is then cooled to about 15° C. and 15.2 g of the reaction product of Part A is added. The resulting deep red mixture is then stirred at ambient temperature for 20 hr and thereafter cooled to about 15° C. After cooling 6.6 g of 3$\alpha$,5$\alpha$-dihydroxy-2$\beta$-(3$\alpha$-hydroxy-trans-1-octenyl)-1$\alpha$-cyclopentane acetaldehyde, $\gamma$-lactol, bis(-tetrahydropyranyl ether) 20 ml of dimethylsulfoxide is added. The resulting mixture is then stirred at ambient temperature for 2.5 hr, diluted with 6 ml of benzene, and shaken with an ice cold solution of 15 g of potassium bisulfate in 300 ml of water and brine. Thereafter the resulting mixture is dried and concentrated under reduced pressure to yield a residue which is triturated with a mixture of diethyl ether in Skellysolve-B. Concentration of the filtrate yields a residue which is thereafter treated with excess ethereal diazomethane. After treatment with acetic acid the resulting organic solution is washed with cold dilute potassium hydroxy, saturated brine, and dried. Concentration under reduced pressure yields a residue which is chromatographed on 2 kg of silica gel, eluting with 4 l of ethyl acetate in Skellysolve-B (1:1). Thereupon 6.35 g of title product is obtained.

C. 2,5-Inter-o-phenylene-3,4-dinor-PGF$_{2\alpha}$, methyl ester (formula XXIII compound).

A mixture of 1.6 g of the reaction product of Part B, 30 ml of acetic acid, 15 ml of water, and 3 ml of tetrahydrofuran is stirred at 40° C. for 4 hr and thereafter diluted with ethyl acetate (400 ml). Washing the resulting solution with a mixture of 30 ml of 50% sodium hdroxide and 300 ml of ice and water, water, and saturated brine, yields a product which is concentrated under reduced pressure to a residue. The residue is then chromatographed on 200 g of silica gel, packed with ethyl acetate (425 ml) and methanol 20 ml). Eluting with 5% methanol in ethyl acetate yields 0.51 g of title product. Characteristic NMR abaorptions are observed at 7.1–7.5, 5.7–6.8, 5.33–5.6, and 3.62$\delta$. The mass spectrum of the trimethylsilyl derivative yields a high resolution molecular ion at 632.3778.

D. 2,5-Inter-o-phenylene-3,4-dinor-5-iodo-6$\beta$-PGI$_1$, methyl ester and 2,5-inter-o-phenylene-3,4-dinor-5,9$\alpha$-epoxy-9-deoxy-6-iodo-PGF$_1$, methyl ester (formula XXIV and XXV compounds, respectively).

To a solution of 4.8 g of the reaction product of Part B and 100 ml of methylene chloride is added 100 ml of saturated sodium bicarbonate. The resulting mixture is then stirred and cooled in an ice bath and a solution containing 4 g of iodine and 200 ml of dichloromethane is added slowly over about 30 min. The resulting mixture is then stirred for 90 min in a cooling bath and thereafter for 165 min at ambient temperature. Thereafter the resulting mixture is then diluted with ethyl acetate and washed with 5% sodium sulfite and brine (200 ml). After drying over sodium sulfate, concentration under reduced pressure yields 5.3 g of a dark brown oil. After dissolution of the oil in 80 ml of an acetic acid-water-tetrahydrofuran mixture (20:10:3) and stirring at 40°–45° C. for 3.5 hr, the resulting mixture is diluted with 800 ml of ethyl acetate and washed with 800 ml of cold 5% sodium hydroxide, 400 ml of water, and 400 ml of brine. Drying over sodium sulfite in concentration under reduced pressure yields 4.15 g of an oil. Dissolution of the oil in 20 ml of dichloromethane in chromatography over 200 g of silica gel eluting with 25–40% acetone in dichloromethane yields the mixture of title products. TLC R$_f$ is 0.23 in 30% acetone in dichloromethane and 0.25 and 0.30 in ethyl acetate. The mass spectrum for the trimethylsilyl derivative exhibits a high resolution peak at 686.2309. NMR absorptions are observed at 7.04–7.44, 5.0–5.73, 3.4–5.0, 3.62, 0.6–3.4, and 0.6–1.03$\delta$.

The mixture of title products contained above may be separated into two fractions (fraction I and fraction II) by the following technique:

The reaction product of Part B (0.50 g) in 25 ml of dichloromethane and 25 ml of saturated aqueous sodium bicarbonate is treated with 0.5 ml of iodine. After stirring in ice water for 90 min, the reaction mixture is diluted with diethyl ether, washed with 10% aqueous sodium sulfite (105 ml) and water (35 ml) and the organic filtrate dried over sodium sulfate. Concentration under reduced pressure to an oil yields a mixture of fractions I and II which are separated on silica gel by the elution of 121 25 ml fractions as follows: 5% Skellysolve B in ethyl acetate (fractions 1–65), ethyl acetate (fractions 66–90), and acetone (fractions 91–121). For fraction I silica gel TLC R$_f$ is 0.49 in 5% methanol in ethyl acetate. Fraction II exhibits silica gel TLC R$_f$ 0.44 in 5% methanol and ethyl acetate. For fraction I the mass spectrum of the trimethylsilyl derivative exhibits a weak molecular ion at 686 and a high resolution peak at 615.1443. For fraction II the mass spectrum of the trimethylsilyl derivative exhibits a high resolution peak at 615.1437. NMR absorptions in deuterochloroform for fraction I are observed at 7.28, 5.60, 5.27, 4.65–3.80, 3.80, 3.69, and 2.70–1.11δ. For fraction II NMR absorptions in deuterochloroform are observed at 7.25, 5.55, 5.30, 4.72–3.90, 3.80, 3.69, 3.66, 2.85–1.11 and 0.90δ.

E. Following the procedure of Part D, but omitting the treatment with acetic acid-water-tetrahydrofuran, the reaction product of Part C is converted to a mixture of the title products of Part D.

F. 2,5-Inter-o-phenylene-3,4-dinor-5,9α-epoxy9-deoxy-PGF$_1$, methyl ester (formula XXVIII) and 2,5-inter-o-phenylene-32,4-dinor-6β-PGI$_1$, methyl ester (formula XXVI).

Nitrogen is bubbled through a solution of 70 mg of the Fraction I product of Part D is 6 ml of methanol for 2–3 min. Thereafter tributyl tin chloride is added dropwise (about 7 drops), while continuing nitrogen bubbling for an additional 2–3 min thereafter. The resulting solution is then stirred under an atmosphere of nitrogen and 70 mg of sodium borohydride is added over 5–10 min. The resulting mixture is then stirred at ambient temperature for about 45 min and thereafter diluted with 45 ml of brine and extracted with ethyl acetate (150 ml). The combined ethyl acetate extracts are then washed with brine (25 ml) and dried over sodium sulfate. Removal of solvent under reduced pressure and dissolving the residue of 2 ml of ethyl acetate yields a mixture of crude title products which is chromatographed on silica gel. Eluting with 1% methanol in ethyl acetate yields 25 mg of the formula XXVII compound and 11 mg of the formula XVI compound.

For 2,5-inter-o-phenylene-3,4-dinor-5,9α-epoxy-9-deoxy-PGF$_1$, methyl ester, silica gel TLC R$_f$ is 0.45 in 5% methanol and ethyl acetate. The mass spectrum for the trimethylsilyl derivative exhibits a high resolution peak at 560.3319. NMR absorptions are observed at 7.25, 5.50, 5.1, 4.3–3.30, 3.78, 3.68, 2.75–1.10 and 0.90δ (deuterochloroform solvent).

For 2,5-inter-o-phenylene-3,4-dinor-PGI$_1$, methyl ester, silica gel TLC R$_f$ is 0.40 in 5% methanol and ethyl acetate. The mass spectrum of the trimethylsilyl derivative exhibits a high resolution peak at 560.3319. NMR absorptions are observed at 7.25, 5.50, 4.6–3.75, 3.71, 3.67, 2.80, 2.75–1.10, and 0.90δ (deuterochloroform solvent).

Alternatively, the fraction II product of Part D (70 mg) is employed in the preparation of the formula XXVI and formula XXVII compounds as follows:

The fraction II product of Part D (70 mg) in 3 ml of methanol is treated with 7 drops of tributyltin in 70 mg of sodium borohydride for 1.5 hr at ambient temperature. After product workup as above, the mixture of crude product is dissolved in 2 ml of dichloromethane and chromatographed over 10 g of silica gel eluting with 15–100% acetone in dichloromethane.

For 2,5-inter-o-phenylene-3,4-dinor-5,9α-epoxy-9-deoxy-PGF$_1$, methyl ester, silica gel TLC R$_f$ is 0.48 is 5% methanol in ethyl acetate. The mass spectrum for the trimethylsilyl derivative exhibits a weak molecular ion at 560 and a high resolution peak at 489.2504. NMR absorptions in deuterochloroform are observed at 7.25, 5.50, 4.45, 4.05, 3.65, 3.66, 2.80–1.0, and 0.90δ.

G. 2,5-Inter-o-phenylene-3,4-dinor-5,9α-epoxy-9-deoxy-6,7-didehydro-PGI$_1$, methyl ester (formula XXVII)

To a solution of 1.0 g of the reaction product of Part D (Fraction II) in 60 ml of toluene is added 3 ml of DBN. The resulting mixture is then stirred at 40°–45° C. for 70 hr. During this time, the reaction mixture is protected from contamination by atmospheric moisture by means of a drying tube. Thereafter an additional 2 ml of DBN is added and stirring and heating are continued for 26 hr. Thereafter the reaction temperature is raised to 80° C. for 4 hr. The reaction at this time being complete, the reaction mixture is cooled, diluted with 50 ml of toluene, and washed with 60 ml of ice water. The water washes are then combined and extracted with 60 ml of diethyl ether and the ethereal extracts are washed with 30 ml of ice water and combined with the toluene solution. After drying of the organic solution over sodium sulfate and evaporation under reduced pressure, a yellow oil (0.50 g) is obtained. Chromatography of the oil on 35 g of silica gel packed with 50% ethyl acetate in Skellysolve-B and eluted with 50–100% ethyl acetate in Skellysolve-B yields 0.41 g of title product. Silica gel TLC R$_f$ is 0.24 in 30% acetone in methylene chloride and 0.28 in ethyl acetate. The mass spectrum of the trimethylsilyl derivative exhibits a high resolution peak at 558.3238. The infrared absorptions are observed at 3380, 1740, 1650, 1495, 1435, 1335, 1295, 1260, 1100, 1055, 1015, 965, and 775 cm$^{-1}$. NMR absorptions are observed at 7.13–7.45, 5.84, 5.46–5.71, 5.12–5.30, 3.5–4.34, 3.65, 2.98, 0.67–2.77, and 0.88δ.

H. 2,5-Inter-o-phenylene-3,4-dinor-5,9α-epoxy-9-deoxy-6,7-didehydro-PGF$_1$

A solution containing 0.11 g of the reaction product of Part G in 2 ml of methanol is diluted with 1 ml of water and 0.10 g of solid sodium carbonate. The resulting mixture is then stirred at ambient temperature for about 19 hr. The resulting mixture is then filtered with diatomaceous earth and a precipitates washed with 10 ml of methanol. The filtrate is then concentrated under reduced pressure until the methanol has been removed and then acidified with 1 ml of 1N potassium bisulfate. The resulting mixture is then diluted with 10 ml of brine and extracted with 45 ml of ethyl acetate. The organic extracts are then washed with brine, back-washed with ethyl acetate and the organic fractions combined, dried over sodium sulfate and concentrated under reduced pressure. The resulting residue, yellow oil (0.10 g), is then dissolved in 1 ml of 10% acetone in dichloromethane and chromatographed over 10 g of acid washed silica gel packed with 10% acetone in dichloromethane. Eluting with 10–40% acetone in dichloromethane yields 56 mg of title product. Silica gel TLC R$_f$ is 0.20 in acetone, dichloromethane, acetic acid (30:70:2). The mass spectrum for the trimethylsilyl derivative exhibits a high resolution peak at 616.3457. NMR absorptions are observed at 7.26, 5.73–6.19, 5.37–5.73, 5.)4–5.27, 3.33–4.33, 0.67–2.83, and 0.87δ.

I. 2,5-Inter-o-phenylene-3,4-dinor-5,9α-epoxy-9-deoxy-PGF$_1$

The formula XXVIII reaction product of Part F (100 mg) and 3 ml of methanol is cooled and stirred in an ice bath under nitrogen atmosphere. Addition of 3 N aqueous potassium hydroxide (2 ml) is followed by stirring in a cooling bath under a nitrogen atmosphere for 5 min. After allowing the reaction mixture to warm to ambient temperature (stirring for about 45 min), the resulting mixture is then diluted with 8 ml of potassium bisulfate, 5 ml of brine and sodium chloride. Extraction with ethyl acetate (45 ml), washing with brine (30 ml), drying over sodium sulfate, concentrating to a residue, and dissolving the residue in dichloromethane (3 ml), chromatographing on 10 g of acid-washed silica gel, packed with 20% acetone in dichloromethane and eluting with 20–30% acetone in dichloromethane yields 53 mg of pure title product. Silica gel TLC $R_f$ is 0.22 in 30% acetone and dichloromethane. The mass spectrum exhibits a high resolution peak at 618.3570. NMR absorptions in deuterochloroform are observed at 7.28, 5.50, 3.62–4.67, 0.69–3.0, and 0.87$\delta$.

J. 2,5-Inter-o-phenylene-3,4-dinor-6$\beta$-PGI$_1$.

Following the procedure of Part I and chromatographing on 10 g of silica gel eluted with 30–40% acetone and dichloromethane yields from 100 mg of the formula XXVI product of Part F 80 mg of title product. Silica gel TLC $R_f$ is 0.15 in 30% acetone in dichloromethane (2% acetic acid added). The mass spectrum of the trimethylsilyl derivative exhibits a high resolution peak at 618.3564. NMR absorptions in deuterochloroform are observed at 7.25, 5.45, 4.55–3.75, 3.70, 2.90, 2.85–1.10 and 0.90$\delta$.

Following the procedures described above in Example 1, there are prepared 2,5-inter-o-phenylene-3,4-dinor-PGF$_{2\alpha}$, 11,15-bis(tetrahydropyranyl) ethers), 2,5-inter-o-phenylene-3,4-dinor-PGF$_{2\alpha}$ compounds 2,5-inter-o-phenylene-3,4-dinor-5-iodo-PGI$_1$ compounds 2,5-inter-o-phenylene-3,4-dinor-5,9$\alpha$-epoxy-9-deoxy-6-iodo-PGF$_1$ compounds.

2,5-inter-o-phenylene-3,4-dinor-6$\beta$-PGI$_1$ compounds, and 2,5-inter-o-phenylene-3,4-dinor-5,9$\alpha$-epoxy-9-deoxy6,7-didehydro-PGF$_1$ compounds in free acid or methyl ester form which exhibit the following side chain substituents:

15-Methyl-;
16-Methyl-;
15,16-Dimethyl-;
16,16-Dimethyl-;
16-Fluoro-
15-Methyl-16-fluoro-;
16,16-Difluoro-;
15-Methyl-16,16-difluoro-;
17-Phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
16,16-Difluoro-;
15-Methyl-16,16-difluoro-;
17-Phenyl-18,19,20-trinor-;
17-(m-trifluoromethylphenyl)-18,19,20-trinor-;
17-(m-chlorophenyl)-18,19,20-trinor-;
17-(p-fluorophenyl)-18,19,20-trinor-;
15-Methyl-17-phenyl-18,19,20-trinor-;
16-Methyl-17-phenyl-18,19,20-trinor-;
16,16-Dimethyl-17-phenyl-18,19,20-trinor-;
16-Fluoro-17-phenyl-18,19,20-trinor-;
16,16-Difluoro-17-phenyl-18,19,20-trinor-;
16-Phenyl-17,18,19,20-tetranor-;
15-Methyl-16-phenyl-17,18,19,20-tetranor-;
16-(m-trifluoromethylphenyl)-17,18,19,20-tetranor-;
16-(m-chlorophenyl)-17,18,19,20-tetranor-;
16-(p-fluorophenyl)-17,18,19,20-tetranor-;
16-Phenyl-18,19,20-trinor-;
15-Methyl-16-phenyl-18,19,20-trinor-;
16-Methyl-16-phenyl-18,19,20-trinor-;
15,16-Dimethyl-16-phenyl-18,19,20-trinor-;
16-Phenoxy-17,18,19,20-tetranor-;
15-Methyl-16-phenoxy-17,18,19,20-tetranor-;
16-(m-trifluoromethylphenoxy)-17,18,19,20-tetranor-;
16-(m-chlorophenoxy)-17,18,19,20-tetranor-;
16-(p-fluorophenoxy)-17,18,19,20-tetranor-;
16-Phenoxy-18,19,20-trinor-;
15-Methyl-16-phenoxy-18,19,20-trinor-;
16-Methyl-16-phenoxy-18,19,20-trinor-;
15,16-Dimethyl-16-phenoxy-18,19,20-trinor-;
13,14-Didehydro-;
16-Methyl-13,14-didehydro-;
16,16-Dimethyl-13,14-didehydro-;
16-Fluoro-13,14-didehydro-;
16,16-Difluoro-13,14-didehydro-;
17-Phenyl-18,19,20-trinor-13,14-didehydro-;
17-(m-trifluoromethylphenyl)-18,19,20-trinor-13,14-didehydro-;
17-(m-chlorophenyl)-18,19,20-trinor-13,14-didehydro-;
17-(p-fluorophenyl)-18,19,20-trinor-13,14-didehydro-;
16-Methyl-17-phenyl-18,19,20-trinor-13,14-didehydro-;
16,16-Dimethyl-17-phenyl-18,19,20-trinor-13,14-didehydro-;
16-Fluoro-17-phenyl-18,19,20-trinor-13,14-didehydro-;
16,16-Difluoro-17-phenyl-18,19,20-trinor-13,14-didehydro-;
16-Phenyl-17,18,19,20-tetranor-13,14-didehydro-;
16-(m-trifluoromethylphenyl)-17,18,19,20-tetranor13,14-didehydro-;
16-(m-chlorophenyl)-17,18,19,20-tetranor-13,14didehydro-;
16-Phenyl-18,19,20-trinor-13,14-didehydro-;
16-Methyl-16-phenyl-18,19,20-trinor-13,14-didehydro-;
16-Phenoxy-17,18,19,20-tetranor-13,14-didehydro-;
16-(m-trifluoromethylphenoxy)-17,18,19,20-tetranor13,14-didehydro-;
16-(m-chlorophenoxy)-17,18,19,20-tetranor-13,14-didehydro-;
16-Phenoxy-18,19,20-trinor-13,14-didehydro-;
16-Methyl-16-phenoxy-18,19,20-trinor-13,14didehydro-;
13,14-Dihydro-;
16-Methyl-13,14-dihydro-;
16,16-Dimethyl-13,14-dihydro-;
16-Fluoro-13,14-dihydro-;
16,16-Difluoro-13,14-dihydro-;
17-Phenyl-18,19,20-trinor-13,14-dihydro-;
17-(m-trifluoromethylphenyl)-18,19,20-trinor-13,14-dihydro-;
17-(m-chlorophenyl)-18,19,20-trinor-13,14-dihydro-;
17-(p-fluorophenyl)-18,19,20-trinor-13,14-dihydro-;
16-Methyl-17-phenyl-18,19,20-trinor-13,14-dihydro-;
16,16-Dimethyl-17-phenyl-18,19,20-trinor-13,14-dihydro-;
16-Fluoro-17-phenyl-18,19,20-trinor-13,14-dihydro-;
16,16-Difluoro-17-phenyl-18,19,20-trionor-13,14-dihydro-;
16-Phenyl-17,18,19,20-tetranor-13,14-dihydro-;
16-(m-trifluoromethylphenyl)-17,18,19,20-tetranor-13,14-dihydro-;
16-(m-chlorophenyl)-17,18,19,20-tetranor-13,14-dihydro-;
16-(p-fluorophenyl)-17,18,19,20-tetranor-13,14-dihydro-;
16-Phenyl-18,19,20-trinor-13,14-dihydro-;
16-Methyl-16-phenyl-18,19,20-trinor-13,14-dihydro-;

16-Phenoxy-17,18,19,20-tetranor-13,14-dihydro-;
16-(m-trifluoromethylphenoxy)-17,18,19,20-tetranor-13,14-dihydro-;
16-(m-chlorophenoxy)-17,18,19,20-tetranor-13,14-dihydro-;
16-(p-fluorophenoxy)-17,18,19,20-tetranor-13,14-dihydro-;
16-Phenoxy-18,19,20-trinor-13,14-dihydro;
16-Methyl-16-phenoxy-18,19,20-trinor-13,14-dihydro-; 13-cis-;
16-Methyl-13-cis;
16,16-Dimethyl-13-cis-;
16-Fluoro-13-cis-;
16,16-Difluoro-13-cis-;
17-Phenyl-18,19,20-trinor-13-cis-;
17-(m-trifluoromethylphenyl)-18,19,20-trinor-13-cis-;
17-(m-chlorophenyl)-18,19,20-trinor-13-cis-;
17-(p-fluorophenyl)-18,19,20-trinor-13-cis-;
16-Methyl-17-phenyl-18,19,20-trinor-13-cis-;
16,16-Dimethyl-17-phenyl-18,19,20-trinor-13-cis-;
16-Fluoro-17-phenyl-18,19,20-trinor-13-cis-;
16,16-Difluoro-17-phenyl-18,19,20-trinor-13-cis-;
16-Phenyl-17,18,19,20-tetranor-13-cis-;
16-(m-trifluoromethylphenyl)-17,18,19,20-tetranor-13-cis-;

EXAMPLE 2

2,5-Inter-o-phenylene-3,4-dinor-5,9α-epoxy-9-deoxy-6,7-didehydro-PGF$_1$, sodium salt.

A solution of 383 mg of the reaction product of Example 1, Part H in 8.5 ml of methanol under a nitrogen atmosphere are treated at 25° C. with a single equivalent (8.8 ml) of 0.1 N sodium methoxide in methanol for 5 hr. The resulting solution is then concentrated under reduced pressure (removing the methyl acetate byproduct), then redissolved in 8.5 ml of methanol and 1.5 ml of water. This solution is then stirred for 12 hr under a nitrogen atmosphere whereupon 10 ml of water is added and the methanol removed under reduced presure. The resulting aqueous solution is then freeze-dried, yielding a residue of pure title product.

EXAMPLE 3

2,5-Inter-o-phenylene-3,4-dinor-5,9α-epoxy-9-deoxy-6,7-didehydro-PGF$_1$, tris(hydroxymethyl)aminomethane salt The title product of Example 2 is acidified with dilute aqueous hydrochloric acid and quickly extracted from the aqueous solution with diethyl ether. The ethereal solution is then combined with stirring with a solution of tris(hydroxymethyl)aminomethane, containing exactly 1 equivalent of this base. The resulting aqueous solution, containing the title salt, is then purified in accordance with the isolation procedure of Example 2, thereby yielding pure title product.

The title product of Example 2 is dissolved in dimethylformamide (DMF) and thereafter there is added an equivalent of methyl iodide. The resulting mixture is then maintained at ambient temperature with stirring for several hours, whereupon silica gel TLC analysis indicates thhe esterification reaction is complete. Thereafter, the reaction mixture is washed successively with water and brine and concentrated to a residue containing pure title methyl ester.

EXAMPLE 4

2,5-Inter-o-phenylene-3,4-dinor-5,9α-epoxy-9-deoxy-6,7-didehydro-PGF$_1$, phenyl ester The title product of Example 2 is dissolved in dimethylformamide and thereafter an equivalent of N-methyl-2-bromopyridium iodide is added with stirring. After several hours, the resulting mixture is combined with one equivalent of phenol in triethylamine and the resulting mixture is maintained at ambient temperature with stirring for several hours. When silica gel TLC analysis indicates the esterification reaction is complete, pure title ester is obtained by purification.

EXAMPLE 5

2,5-Inter-o-phenylene-3,4,17,18,19,20-hexanor-5,9α-epoxy-9-deoxy-6,7-didehydro-16-phenoxy-PGF$_1$ and its methyl ester.

Following the procedure of Example 1, Parts B and C, 3α,5α-dihydroxy-2γ-(3α-hydroxy-4-phenoxy-trans-1-butenyl)-1α-cyclopentaneacetaldehyde, γ-lactol, bis(-tetrahydropyranyl ether), 5.4 g, is transformed to 3.97 g of 2,5-inter-o-phenylene-16-phenoxy-3,4,17,18,19,20-hexanor-PGF$_{2α}$, methyl ester. Following the procedure of Example D of Part 1, the preceding compound is transformed to 2,5-inter-o-phenylene-16-phenoxy-3,4,17,18,19,20-hexanor-5,9α-epoxy-9-deoxy-6-iodo-PGF$_1$, methyl ester, 1.29 g. The mass spectrum for the trimethylsilyl derivative exhibits a weak molecular ion at 722, a demethylated high resolution peak at 707.1747 and other peaks at 682, 615, 594, 561, 525, 487, and 397. Characteristic infrared absorptions are observed at 3360, 1735, 1600, 1585, 1495, 1245, 1080, 1040, 1020, 970, 755, and 690 cm$-1$.

The preceding reaction product (0.25 g) is then dehydroiodinated according to the procedure of Example 1, Part F, yielding 2,5-inter-o-phenylene-16-phenoxy-3,4,17,18,19,20-hexanor-5,9α-epoxy-9-deoxy-6,7-didehydro-PGF$_1$, methyl ester (90 mg) as a colorless oil. The mass spectrum for the trimethylsilyl derivative exhibits a high resolution peak at 594.2832 and other peaks at 579, 563, 504, 500, 487, 473, 469, 414, 397, 379, and 243. Hydrolysis of the 200 mg sample of the above methyl ester yields 110 mg of the corresponding acid, 2,5-inter-o-phenylene-16-phenylene-3,4,17,18,19,20-hexanor 5,9α-epoxy-9-deoxy-6,7-didehydro-PGF$_1$. The mass spectrum for the trimethylsilyl derivative exhibits a high resolution peak at 652.3045 and other peaks at 637, 562, 545, 455, 437, 365, and 243.

EXAMPLE 6

2,5-Inter-o-phenylene-3,4-dinor-16,16-difluoro-5,9α-epoxy-9-deoxy-6,7-didehydro-PGF$_1$ and its methyl ester Following the procedure described in Example 5, there are successively prepared from 3α,5α-dihydroxy-2β-(3α-hydroxy-4,4-difluoro-trans-1-octenyl)-1α-cyclopentaneacetaldehyde, γ-lactol, 11,15-bis(tetrahydropyranyl ether), (4.8 g), the following products:

(a) 2,5-inter-o-phenylene-3,4-dinor-16,16-difluoro-PGF$_{2α}$, 11,15-bis(tetrahydropyranyl ether), methyl ester, 5.)4 g as a yellow oil; the mass spectrum for the trimethylsilyl derivative exhibiting a weak molecular ion at 722 and a high resolution peak at 707.1888;

(b) 2,5-inter-o-phenylene-3,4-dinor-16,16-difluoro-5,9α-epoxy-9-deoxy-6-iodo-PGF$_1$, methyl ester, 1.64 g from 4.0 g of the reactant of Part (a);

(c) 2,5-inter-o-phenylene-3,4-dinor-16,16-difluoro-5,9α-epoxy-9-deoxy-6,7-didehydro-PGF$_1$, methyl ester, 70 mg from 250 mg of the reactant of Part (b); the mass spectrum for the trimethylsilyl derivative exhibiting a high resolution peak of 594.2292 and other peaks at 579, 563, 521, 504, 487, 414, 397, and 243;

(d) 2,5-inter-o-phenylene-3,4-dinor-16,16-difluoro-5,9α-epoxy-9-deoxy-6,7-didehydro-PGF$_1$, 320 mg from 520 mg of the reactant of Part (c); the mass spectrum for the trimethylsilyl derivative exhibits a high resolution peak at 652.3240.

EXAMPLE 7

2,5-Inter-o-phenylene-3,4-dinor-16,16-dimethyl-5,9α-epoxy-9-deoxy-6,7-didehydro-PGF$_1$, methyl ester Following the procedure described in Example 1, there are successively prepared from 3α, 5α-dihydroxy-2β-(3α-hydroxy-4,4-dimethyl-trans-1-octenyl)-1α-cyclopentaneacetaldehyde, γ-lactol, 11,15-bis(tetrahydropyranyl ether), the following products;

(a) 2,5-inter-o-phenylene-3,4-dinor-16,16-dimethyl-PGF$_{2\alpha}$, 11,15-bis(tetrahydropyranyl ether), methyl ester;

(b) 2,5-inter-o-phenylene-3,4-dinor-16,16-dimethyl-5,9α-epoxy-9-deoxy-6-iodo-PGF$_1$, methyl ester, 1.08 g from 2.4 g of the reactant of Part (a). Silica gel TLC R$_f$ is 0.33 in 30% acetone and dichloromethane. The mass spectrum of the trimethylsilyl derivative exhibits a weak molecular ion at 714 and a high resolution peak at 699.2371. Infrared absorptions are observed at 3424, 1737, 1607, 1495, 1258, 1189, 1155, 1101, 1069, 1045, 1017, 971, and 758 cm−1.

(c) 2,5-inter-o-phenylene-3,4-dinor-16,16-dimethyl-5,9α-epoxy-9-deoxy-6,7-didehydro-PGF$_1$, methyl ester, 0.32 g from 1.0 g of the reactant of Part (b); the mass spectrum for the trimethylsilyl derivative exhibiting a high resolution peak at 571.3287. Silica gel TLC R$_f$ is 0.34 in 30% acetone and dichloromethane. NMR absorptions are observed at 7.3, 5.90, 5.60, 5.20, 4.20, 4.00–3.50, 3.67, 2.90, 2.80–1.10, 0.90, and 0.88δ (deuterochloroform solvent).

EXAMPLE 8

2,5-Inter-o-phenylene-3,4-dinor-5,9α-epoxy-9-deoxy-6,7-didehydro-PGF$_1$, sec-butyl ester.

To a stirred solution of 0.16 g of the reaction product of Example 1, Part G, in 5 ml of methylene chloride is added 0.07 g of triethylamine and 55 mg of isobutyl chloroformate. The solution is stirred for 30 min at ambient temperature (protected from moisture by a drying tube). Thereafter 55 mg of p-hydroxyacetophenone is added and stirring is continued at ambient temperature for 90 min. Elution of the resulting mixture with 30 ml of dicloromethane followed by washing with 10 ml of water, 10 ml of 0.1 N aqueous sodium hydroxide and 15 ml of water yields a solution which is dried over sodium sulfate and concentrated under reduced pressure to a residue. Dissolving the residue in 3 ml of dichloromethane and chromatographing over 20 g of acid-washed silica gel, eluting with 5–30% acetone in dichloromethane yields pure title product (0.10 g). Silica gel TLC R$_f$ is 0.53 in 30% acetone and dichloromethane (2% acetic acid added). The mass spectrum of the trimethylsilyl derivative exhibits a high resolution peak at 600. NMR absorptions in deuterochloroform are observed at 7.27, 5.84, 5.4–5.75, 5.15–5.4, 3.55–4.34, 0.90, and 0.79δ.

FORMULAS

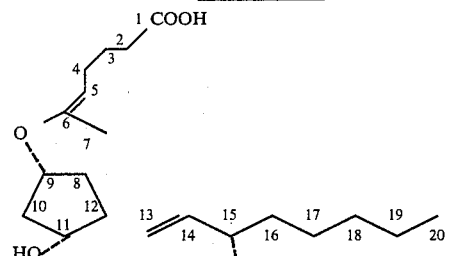

I

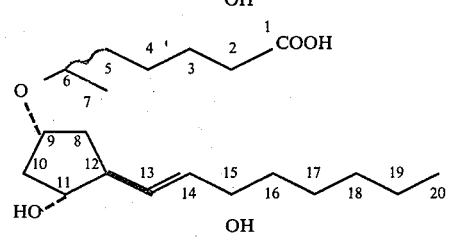

II

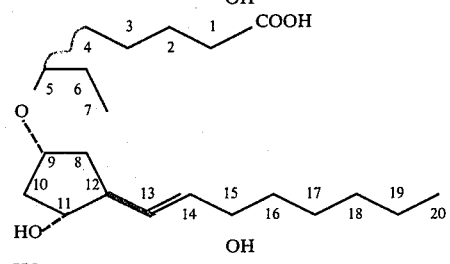

III

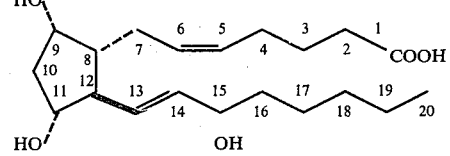

IV

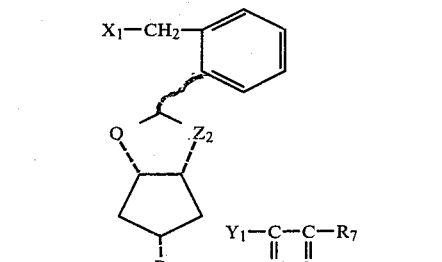

V

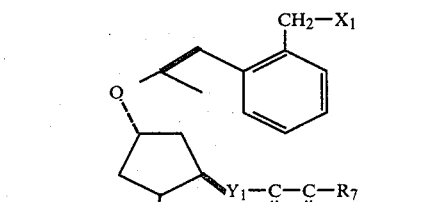

VI

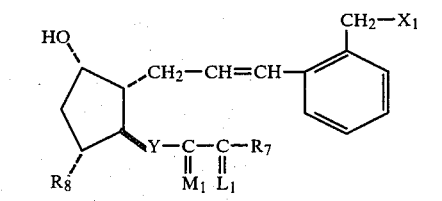

VII

-continued
FORMULAS

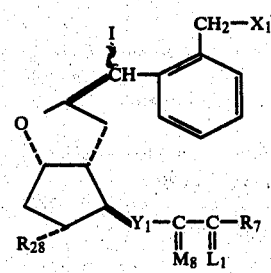

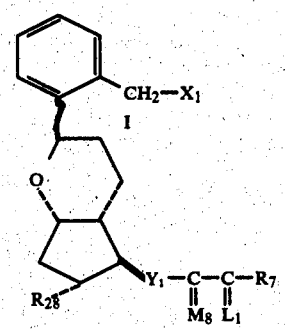

CHART A

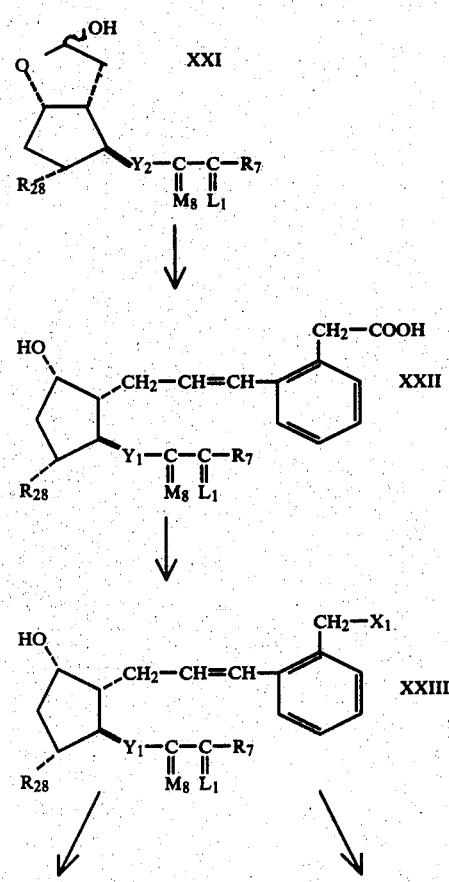

-continued
CHART A

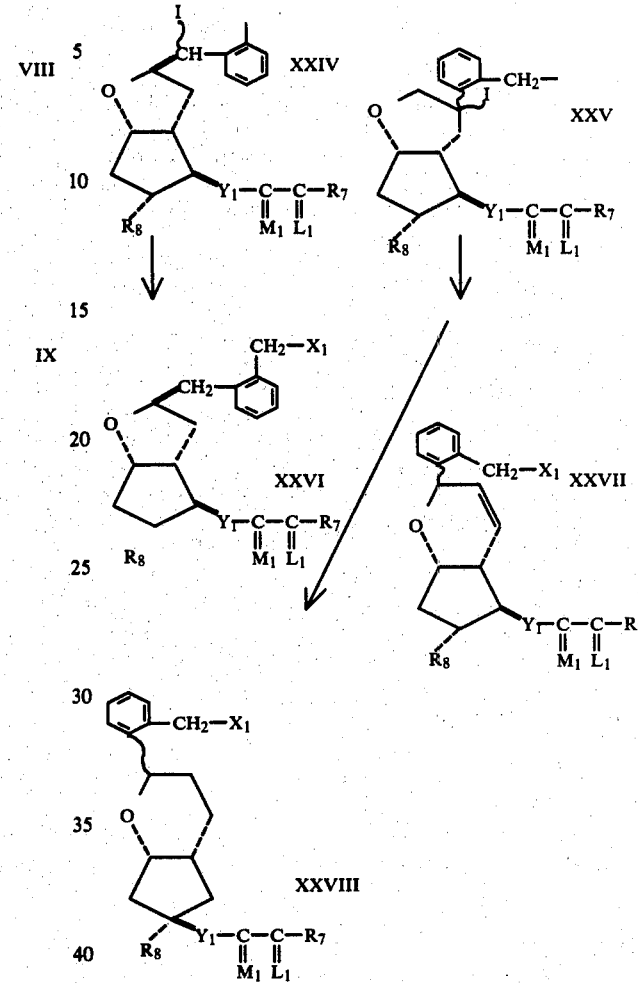

We claim:
1. A prostacyclin intermediate of formula VII

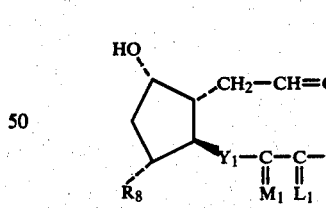

wherein
$R_8$ is hydrogen, hydroxy, or hydroxymethyl;
wherein $Y_1$ is
(1) trans—CH=CH—,
(2) cis—CH=CH—,
(3) —CH$_2$CH$_2$—, or
(4) —C≡C—,
wherein $M_1$ is α-$R_5$:β-OH or αOH-β-$R_5$, wherein $R_5$ is hydrogen or alkyl with one to 4 carbon atoms, inclusive,
wherein $L_1$ is α$R_3$:β-$R_4$, α-$R_4$:β-$R_3$, or a mixture of α-$R_3$:β-$R_4$ and α$R_4$:β-$R_3$, wherein $R_3$ and $R_4$ are hydrogen, methyl, or fluoro, being the same or different, with the proviso that one of $R_3$ and $R_4$ is fluoro only when the other is hydrogen or fluoro;

wherein $R_7$ is
(1) $-(CH_2)_m-CH_3$, wherein m is an integer from one to 5, inclusive;
(2) phenoxy;
(3) phenoxy substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
(4) phenyl;
(5) phenyl substituted by one, 2 or 3 chloro, fluoro, trifluoromethyl, alkyl of one to 3 carbon atoms, inclusive, or alkoxy of one to 3 carbon atoms, inclusive, with the proviso that not more than two substituents are other than alkyl;
(6) phenylmethyl, phenylethyl, or phenylpropyl; or
(7) phenylmethyl, phenylethyl, or phenylpropyl substituted by one, two or three chloro, fluoro, trifluoromethyl, alkyl or one to 3 carbon atoms, inclusive, or alkoxy of one to 3 carbon atoms, inclusive, or alkoxy of one to 3 carbon atoms, inclusive, with the proviso that not more than two substituents are other than alkyl; with the proviso that $R_7$ is phenoxy or substituted phenoxy, only when $R_3$ and $R_4$ are hydrogen or methyl, being the same or different;

wherein $R_1$ is
(1) hydrogen;
(2) alkyl of one to 12 carbon atoms, inclusive;
(3) cycloalkyl of 3 to 10 carbon atoms, inclusive;
(4) aralkyl of 7 to 12 carbon atoms, inclusive;
(5) phenyl;
(6) phenyl substituted with one, 2 or 3 chloro or alkyl of one to 3 carbon atoms;
(7) phenyl substituted in the para position by
  (a) $-NH-CO-R_{25}$,
  (b) $-CO-R_{26}$,
  (c) $-O-CO-R_{27}$, or
  (d) $-CH=N-NH-CO-NH_2$, wherein $R_{25}$ is methyl, phenyl, acetamidophenyl, benzamidophenyl, or $-NH_2$; $R_{26}$ is hydroxy, methyl, phenyl, $-NH_2$, or methoxy; and $R_{27}$ is phenyl or acetaminophenyl, inclusive, or a pharmacologically acceptable salt thereof when $R_1$ is hydrogen.

* * * * *

UNITED STATES PATENT OFFICE
CERTIFICATE OF CORRECTION

Patent No. 4,289,893  Dated 15 September 1981

Inventor(s) Udo F. Axen, et al.

It is certified that error appears in the above-identified patent and that said Letters Patent are hereby corrected as shown below:

Column 1, lines 26-33, that portion of the formula reading

 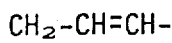     should read     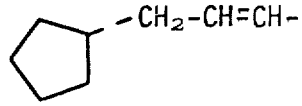

Column 2, line 34, should read -- APPENDIX A --;

Column 4, line 50, "(4) $-CH\equiv C-$," should read -- (4) $-C\equiv C-$, --

Column 21, line 17, "inter-o-phenylene-32,4-" should read -- inter-o-phenylene-2,4- --;

Column 26, line 27, "Example D of Part 1" should read -- Part D of Example 1 --; line 66, "5.)4 g" should read -- 5.04 g --.

Column 28, lines 5-61,
Formulas I, II, III, IV, V, and VI should read as follows instead of as appears in the printed patent:

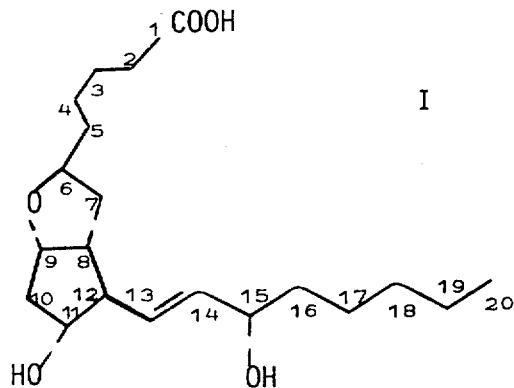

I

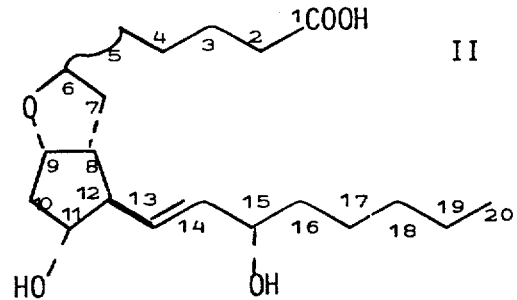

II

Page 2 of 4 Pages

UNITED STATES PATENT OFFICE
CERTIFICATE OF CORRECTION

Patent No. 4,289,893            Dated  15 September 1981

Inventor(s)  Udo F. Axen, et al.

It is certified that error appears in the above-identified patent and that said Letters Patent are hereby corrected as shown below:

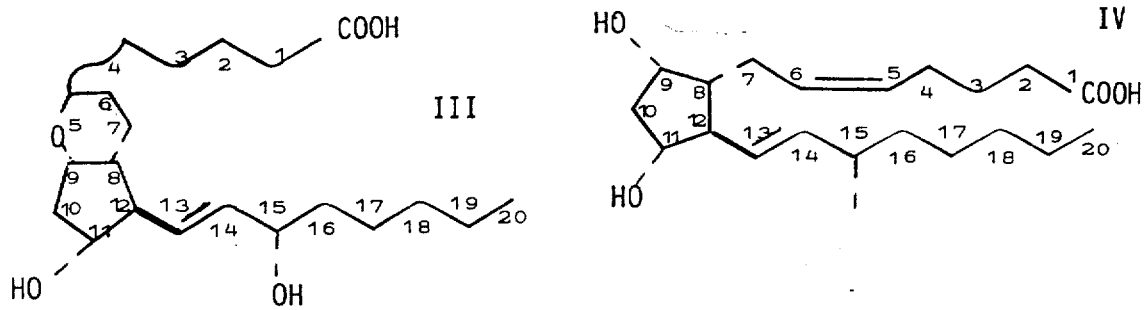

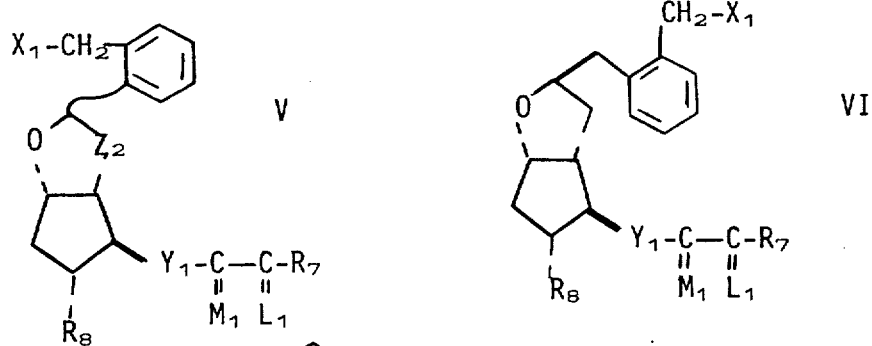

Column 29, lines 16-29, should read

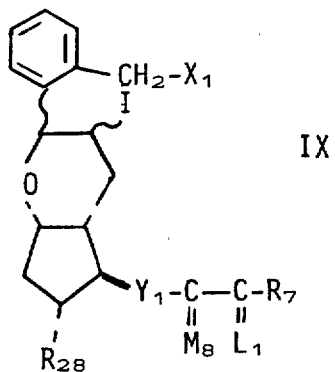

UNITED STATES PATENT OFFICE
CERTIFICATE OF CORRECTION

Patent No. 4,289,893          Dated 15 September 1981

Inventor(s) Udo F. Axen, et al.

It is certified that error appears in the above-identified patent and that said Letters Patent are hereby corrected as shown below:

Column 30, lines 3-15, should read as follows:

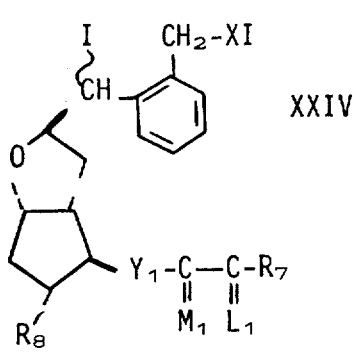

XXIV

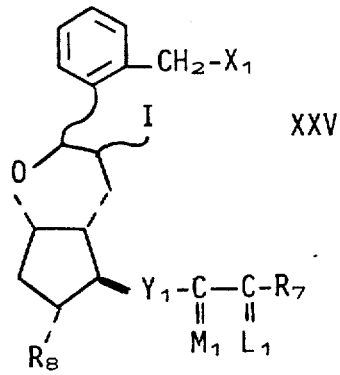

XXV

Column 30, lines 17-29, should read:

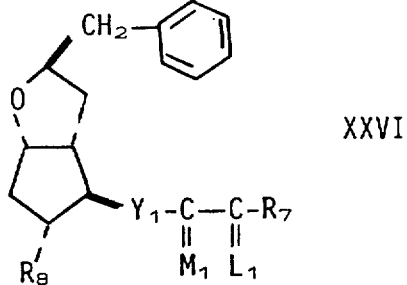

XXVI

UNITED STATES PATENT OFFICE
CERTIFICATE OF CORRECTION

Patent No. 4,289,893　　　　　Dated 15 September 1981

Inventor(s) Udo F. Axen, et al.

It is certified that error appears in the above-identified patent and that said Letters Patent are hereby corrected as shown below:

Column 30, line 66, "$\alpha OH\text{-}\beta\text{-}R_5$" should read -- $\alpha\text{-}OH\text{:}\beta\text{-}R_5$ --;

Column 31, lines 22-24, ", or alkoxy of one to 3 carbon atoms, inclusive, or alkoxy of one to 3 carbon atoms, inclusive," should read -- , or alkoxy of one to 3 carbon atoms, inclusive, --

Signed and Sealed this

Thirteenth Day of April 1982

|SEAL|

Attest:

Attesting Officer

GERALD J. MOSSINGHOFF
Commissioner of Patents and Trademarks